(12) United States Patent
Gumina et al.

(10) Patent No.: US 7,897,759 B2
(45) Date of Patent: Mar. 1, 2011

(54) METABOLICALLY STABLE PUROMYCIN ANALOGS

(75) Inventors: Giuseppe Gumina, Savannah, GA (US); Roger L. White, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 365 days.

(21) Appl. No.: 12/164,900

(22) Filed: Jun. 30, 2008

(65) Prior Publication Data
US 2009/0069556 A1    Mar. 12, 2009

Related U.S. Application Data

(60) Provisional application No. 60/937,679, filed on Jun. 29, 2007.

(51) Int. Cl.
*C07H 19/00*    (2006.01)
*C07H 19/22*    (2006.01)

(52) U.S. Cl. ............... 536/27.13; 536/27.1; 536/27.14; 536/27.7; 536/27.21; 536/27.22; 536/27.23; 536/27.3

(58) Field of Classification Search ............ None
See application file for complete search history.

(56) References Cited

PUBLICATIONS

Starck et al. JACS (2003), vol. 125, pp. 8090-8091.*

* cited by examiner

*Primary Examiner*—Patrick T Lewis
(74) *Attorney, Agent, or Firm*—Pabst Patent Group LLP

(57) ABSTRACT

Disclosed are structurally modified, metabolically stable nucleosides having antitumor activity wherein the formation of toxic metabolites is blocked and antimicrobial activity. The disclosure further relates to pharmaceutical compositions comprising one or more disclosed modified nucleosides and to methods of use thereof.

23 Claims, 4 Drawing Sheets

METABOLICALLY STABLE PUROMYCIN ANALOGS

This application claims benefit of priority to U.S. Provisional No. 60/937,679, filed Jun. 29, 2007, entitled "METABOLICALLY STABLE PUROMYCIN ANALOGS" which is incorporated herein by reference in its entirety.

FIELD OF THE DISCLOSURE

The present disclosure relates to structurally modified nucleosides having antitumor activity wherein the formation of toxic metabolites is blocked. The disclosure further relates to pharmaceutical compositions comprising one or more of the disclosed modified nucleosides and to methods of use thereof.

BACKGROUND

Naturally occurring peptidyl nucleosides have long been investigated as antitumor as well as antimicrobial agents. Among those known for having these properties are cryschandin (Yamashita, M. et al., Chryscandin, A novel peptidyl nucleoside antibiotic. I. Taxonomy, fermentation, isolation and characterization. *J. Antibiotics* (1984), 37:1279-1283), L-homocitrullylaminoadenosine (Kredich, N. M. et al., Homocitrullyl-aminoadenosine, a nucleoside isolated from *Cordyceps militaris*. *J. Biol. Chem*. (1961) 236:3300-3302), L-lysylamino-adenosine (Shiao, M. et al., Natural products in *Cordyceps*. *Proc. Natl. Sci. Counc. ROC(A)* (1989) 13:382-387), and the more recently discovered cystocin (Lee, H. et al., Cystocin, a novel antibiotic, produced by *Streptomyces* sp. GCA0001: biological activities. *Arch. Pharm. Res*. (2003) 26:446-448).

Puromycin, produced by *Streptomyces alboniger*, is the best known member of this class. It mimics the aminoacyl-adenyl terminus of aminoacyl-tRNA, acting as a substrate of peptidyl transferase (Herris, R. J. et al., Molecular mechanism of protein biosynthesis. Ed. Weissbach, H.; and Pestka, S., Academic Press Inc, 413-442 (1977); Harris, R. J. et al., Peptide bond formation on the ribosome. Structural requirements for inhibition of protein synthesis and of release of peptides from peptidyl-tRNA on bacterial and mammalian ribosome by aminoacyl and nucleotidyl analogues of puromycin. *Biochim. Biophys. Acta* (1971) 240:244-262). Puromycin's incorporation into the growing peptide causes the growing chain to terminate prematurely, releasing an incomplete protein.

A number of natural peptidyl nucleoside antibiotics share similar properties with puromycin. Widely used as a basic tool in biochemistry and molecular biology, puromycin has been evaluated as an antimicrobial and antitumor agent with disappointing results. As an anticancer agent, the major drawback of puromycin is characteristic nephrotoxicity due to metabolism to puromycin amino nucleoside (PAN) (Borowsky, B. A. et al., Structural analogues of puromycin in production of experimental nephrosis in rats. *Proc. Soc. Exp. Biol. Med*. (1958) 97:857-860), which is demethylated in the liver (Derr, R. F. et al., Metabolism of puromycin aminonucleoside in the normal, "pre-nephrotic," and nephrotic rat. *Proc. Soc. Exp. Biol. Med*. (1967) 125:248-252; Dickie, N. et al., Inhibition of adenosine deaminase by a metabolite of the nephrotoxic drug, puromycin aminonucleoside. *Proc. Soc. Exp. Biol. Med*. (1966) 123:421-423) and then phosphorylated to the toxic metabolite 3'-amino-3'-deoxy-$N^6$-methyladenosine phosphate (Kmetec, E. et al., Metabolism of puromycin aminonucleoside in the rat. Formation of nucleotide derivatives. *Biochem. Pharmacol*. (1970) 19:1493-1500).

What are needed are metabolically stable, modified peptidyl nucleosides that have anti-tumor activity but that are metabolically stable and pharmaceutical compositions comprising the modified nucleosides.

SUMMARY

In accordance with the purposes of the disclosed materials, compounds, compositions, and methods, as embodied and broadly described herein, the disclosed matter, in one aspect, relates to compositions and methods for preparing and using such compositions. In another aspect, disclosed herein are metabolically stable nucleoside analogs suitable for use as, inter alia, anti-tumor agents for the treatment of cancer. Further disclosed herein are pharmaceutical compositions comprising one or more of the disclosed compounds. In addition, the present disclosure relates to methods for modifying natural peptidyl nucleosides such that their toxicity is reduced without affecting their ability to retain antitumor or antimicrobial activity. Also disclosed herein are methods for treating cancer. Also disclosed herein are methods for killing or inhibiting the growth of microbes such as bacteria, fungi, or viruses.

The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE FIGURES

The accompanying figures, which are incorporated in and constitute a part of this specification, illustrate several aspects described below

DETAILED DESCRIPTION

Figure 1:
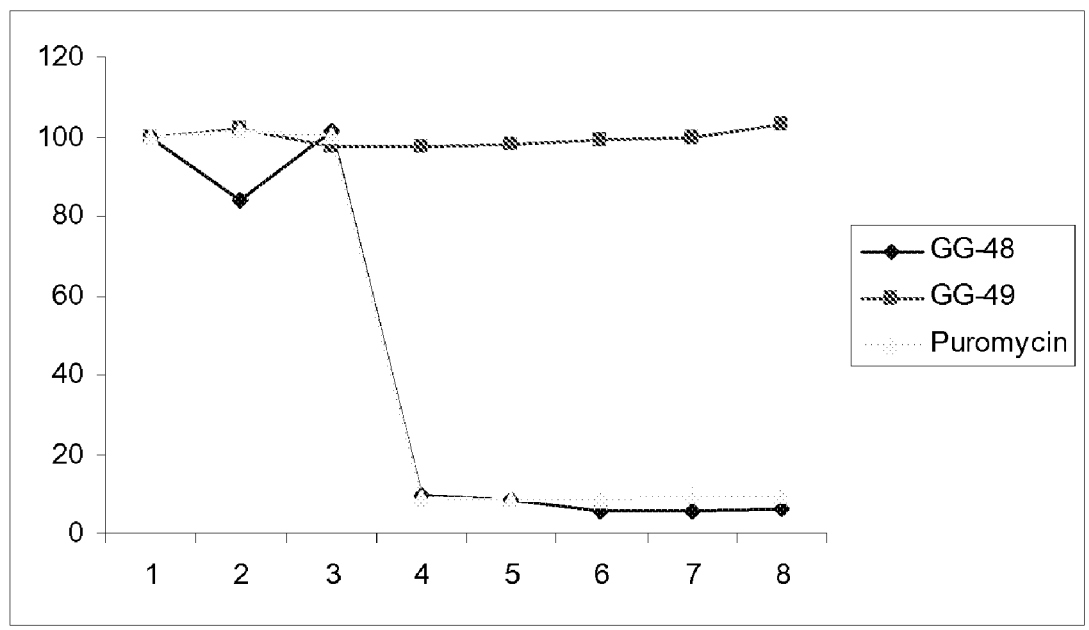
FIG. 1 is a graph of cytotoxic activity for 9-{3-[1-(3-amino-2-oxo-4-phenyl)butyl]-3-deoxy-D-ribofuranosyl}-6-dimethylaminopurine) ("GG-48") versus puromycin and control in breast cancer (MCF-7) cells.
Figure 2:
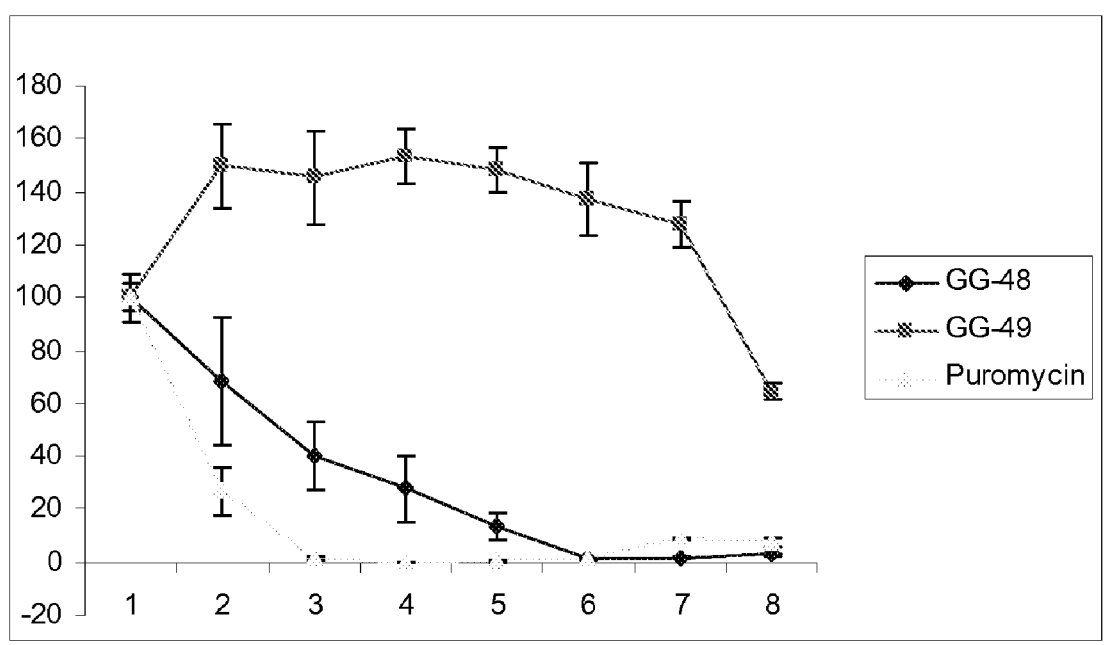
FIG. 2 is a graph of cytotoxic activity of 9-{3-[1-(3-amino-2-oxo-4-phenyl)butyl]-3-deoxy-D-ribofuranosyl}-6-dimethylaminopurine) ("GG-48") versus puromycin and control in leukemia (HL-60) cells.

The materials, compositions, articles, devices, and methods described herein may be understood more readily by reference to the following detailed description of specific aspects of the disclosed subject matter, and methods and the Examples included therein and to the Figures and their previous and following description.

Before the present materials, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed subject matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

As used in the specification and the appended claims, the singular forms "a," "an," and "the" include plural referents unless the context clearly dictates otherwise. Thus, for example, reference to "a compound" includes mixtures of two or more such compounds, reference to "an agent" includes mixtures of two or more such agents, reference to "the composition" includes mixtures of two or more such compositions, and the like.

Throughout the specification and claims, the word "comprise" and variations of the word, such as "comprising" and "comprises," means "including but not limited to," and is not intended to exclude, for example, other additives, components, integers, or steps.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Chemical Definitions

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The term "hydrocarbyl" stands for any carbon atom-based unit (organic molecule), said units optionally containing one or more organic functional groups, including inorganic atom comprising salts, inter alia, carboxylate salts and quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (carbocyclic and aryl rings) or can comprise one or more heteroatoms in the ring (heterocyclic and heteroaryl). For "carbocyclic" rings, the lowest number of carbon atoms in a ring is 3, i.e., cyclopropyl. For "aryl" rings, the lowest number of carbon atoms in a ring is 6, i.e., phenyl. For "heterocyclic" rings, the lowest number of carbon atoms in a ring is 1, i.e., diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein. Substituted and unsubstituted linear, branched, or cyclic alkyl units include the following non-limiting examples: methyl $(C_1)$, ethyl $(C_2)$, n-propyl $(C_3)$, iso-propyl $(C_3)$, cyclopropyl $(C_3)$, n-butyl $(C_4)$, sec-butyl $(C_4)$, iso-butyl $(C_4)$, tert-butyl $(C_4)$, cyclobutyl $(C_4)$, cyclopentyl $(C_5)$, cyclohexyl $(C_6)$, and the like. Substituted linear, branched, or cyclic alkyl, include the following non-limiting examples: hydroxymethyl $(C_1)$, chloromethyl $(C_1)$, trifluoromethyl $(C_1)$, aminomethyl $(C_1)$, 1-chloroethyl $(C_2)$, 2-hydroxyethyl $(C_2)$, 1,2-difluoroethyl $(C_2)$, 2,2,2-trifluoroethyl $(C_3)$, 3-carboxypropyl $(C_3)$, 2,3-dihydroxycyclobutyl $(C_4)$, and the like.

Substituted and unsubstituted linear, branched, or cyclic alkenyl include ethenyl $(C_2)$, 3-propenyl $(C_3)$, 1-propenyl (also 2-methylethenyl) $(C_3)$, isopropenyl (also 2-methylethen-2-yl) $(C_3)$, buten-4-yl $(C_4)$, and the like. Substituted linear or branched alkenyl, include the following non-limiting examples: 2-chloroethenyl (also 2-chlorovinyl) $(C_2)$, 4-hydroxybuten-1-yl $(C_4)$, 7-hydroxy-7-methyloct-4-en-2-yl $(C_9)$, 7-hydroxy-7-methyloct-3,5-dien-2-yl $(C_9)$, and the like.

Substituted and unsubstituted linear or branched alkynyl include ethynyl $(C_2)$, prop-2-ynyl (also propargyl) $(C_3)$, propyn-1-yl $(C_3)$, and 2-methyl-hex-4-yn-1-yl $(C_7)$; substituted linear or branched alkynyl, non-limiting examples of which include, 5-hydroxy-5-methylhex-3-ynyl $(C_7)$, 6-hydroxy-6-methylhept-3-yn-2-yl $(C_8)$, 5-hydroxy-5-ethylhept-3-ynyl $(C_9)$, and the like.

The term "aryl" is defined herein as encompassing unsubstituted phenyl $(C_6)$, naphthylen-1-yl $(C_{10})$, naphthylen-2-yl ($C_{10}$), or substituted phenyl ($C_6$), naphthylen-1-yl ($C_{10}$), naphthylen-2-yl ($C_{10}$), non-limiting examples of which include 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

The terms "heterocyclic" and/or "heterocycle" are defined herein as "cyclic units comprising one or more heteroatoms chosen from nitrogen (N), oxygen (O), or sulfur (S), or mixtures of N, O, and S, and wherein further the ring is not a heteroaryl ring as defined herein below." The following are non-limiting examples of heterocyclic rings: aziridinyl ($C_2$), azetidinyl ($C_3$), tetrahydrofuranyl ($C_4$), morpholinyl ($C_4$), piperazinyl ($C_4$), piperidinyl ($C_4$), tetrahydropyranyl ($C_5$), and the like.

The following are non-limiting examples of units that can substitute for hydrogen atoms on a hydrocarbyl or other unit:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_1$-$C_9$ heterocyclic rings; as described herein below;

iv) substituted or unsubstituted $C_1$-$C_9$ heteroaryl rings; as described herein below;

v) —$(CR^{52a}R^{52b})_zOR^{51}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vi) —$(CR^{52a}R^{52b})_zC(O)R^{51}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;

vii) —$(CR^{52a}R^{52b})_zC(O)OR^{51}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

viii) —$(CR^{52a}R^{52b})_zC(O)N(R^{51})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

ix) —$(CR^{52a}R^{52b})_zN(R^{51})_2$; for example, —$NH_2$, —$CH_2NH_2$, —$NHCH_3$, —$N(CH_3)_2$, —$NH(CH_2CH_3)$, —$CH_2NHCH_3$, —$CH_2N(CH_3)_2$, and —$CH_2NH(CH_2CH_3)$;

x) halogen; —F, —Cl, —Br, and —I;

xi) —$(CR^{52a}R^{52b})_zCN$;

xii) —$(CR^{52a}R^{52b})_zNO_2$;

xiii) —$CH_jX_k$; wherein X is halogen, j is from 0 to 2, j+k=3; for example, —$CH_2F$, —$CHF_2$, —$CF_3$, —$CCl_3$, or —$CBr_3$;

xiv) —$(CR^{52a}R^{52b})_zSR^{51}$; —SH, —$CH_2SH$, —$SCH_3$, —$CH_2SCH_3$, —$SC_6H_5$, and —$CH_2SC_6H_5$;

xv) —$(CR^{52a}R^{52b})_zSO_2R^{51}$; —$SO_2H$, —$CH_2SO_2H$, —$SO_2CH_3$, —$CH_2SO_2CH_3$, —$SO_2C_6H_5$, and —$CH_2SO_2C_6H_5$; and xiii) —$(CR^{52a}R^{52b})_zSO_3R^{51}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{51}$ is independently hydrogen, substituted or unsubstituted $C_1$-$C_4$ linear, branched, or cyclic alkyl, phenyl, benzyl; or two $R^{51}$ units can be taken together to form a ring comprising 3-7 atoms; $R^{52a}$ and $R^{52b}$ are each independently hydrogen or $C_1$-$C_4$ linear or branched alkyl; the index p is from 0 to 4.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Reference will now be made in detail to specific aspects of the disclosed materials, compounds, compositions, components, devices, articles, and methods, examples of which are illustrated in the following description and examples, and in the figures and their previous and following description.

Compositions

The present disclosure relates to metabolically stable nucleosides wherein the —NH— unit (amino) of the amide linkage of naturally occurring nucleosides, for example, puromycin, is replaced by a —$CH_2$— unit (methylene) linkage. Naturally occurring peptidyl nucleosides such as puromycin are metabolized by the following scheme:

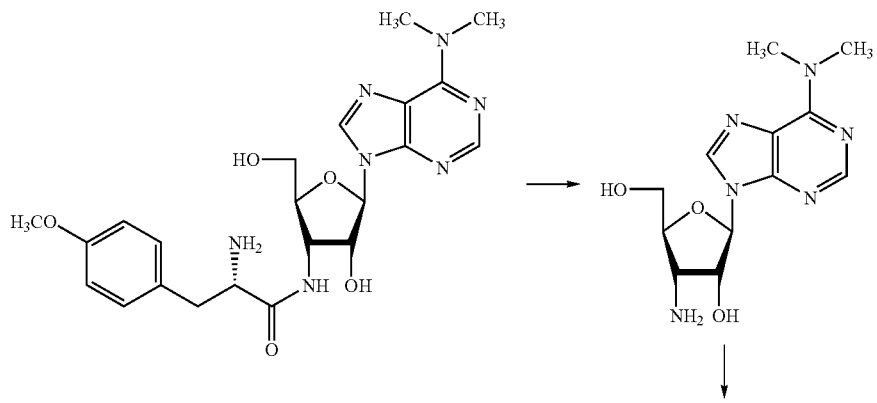

-continued

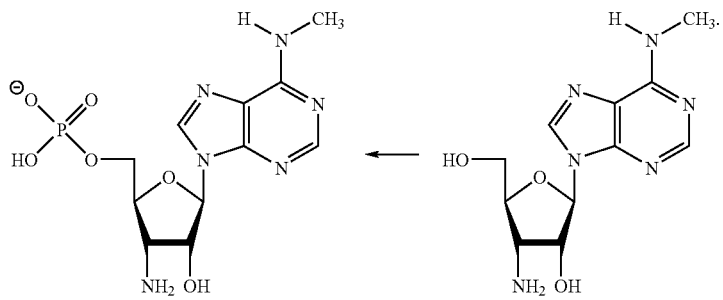

In this process, the toxic metabolite 3'-amino-3'-deoxy-$N^6$-methyladenosine phosphate is released. The metabolically stable compounds of the present disclosure are stable towards this metabolism as indicated in the following scheme:

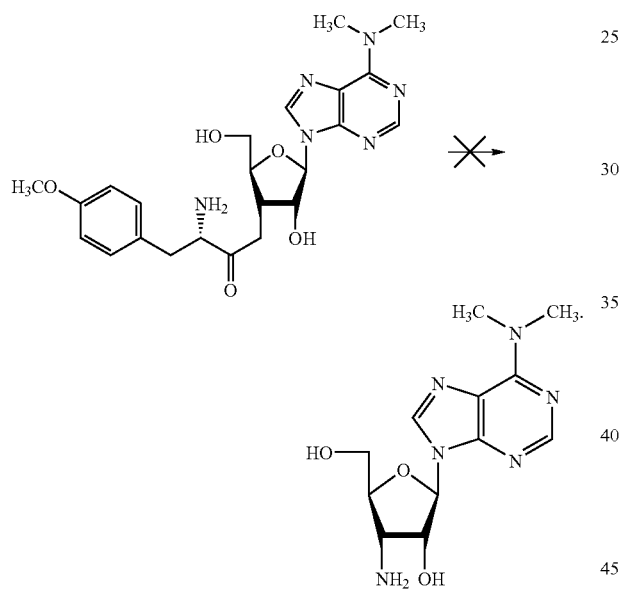

As such, the compounds of the present disclosure are metabolically stable nucleosides having the following general formula:

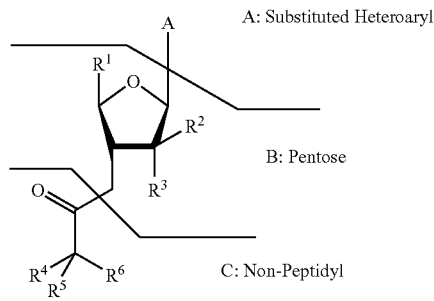

wherein the compounds comprises a substituted heteroaryl unit (A), a pentose unit (B), and a non-peptidyl unit (C).

In the formula, "A" represents a $C_5$-$C_8$ heteroaryl unit. Non-limiting examples of "A" in the above formula include 1H-indolyl, 1H-pyrrolo[2,3-b]pyridinyl, 7H-pyrrolo[2,3-d]pyrimidinyl, 5H-pyrrolo[2,3-b]pyrazinyl, 7H-pyrrolo[2,3-c]pyridazinyl, 5H-pyrrolo[3,2-c]pyridazinyl, 1H-benzo[d]imidazolyl, 7H-imidazo[4,5-c]pyridazinyl, 1H-imidazo[4,5-b]pyrazinyl, 7H-purinyl, 9H-purinyl, quinolin-2-yl, quinolin-3-yl, quinolin-4-yl, isoquinolin-1-yl, isoquinolin-3-yl, and isoquinolin-4-yl.

The pentose unit of the disclosed compounds can have any substitutions as disclosed herein along the pentose ring, for example:

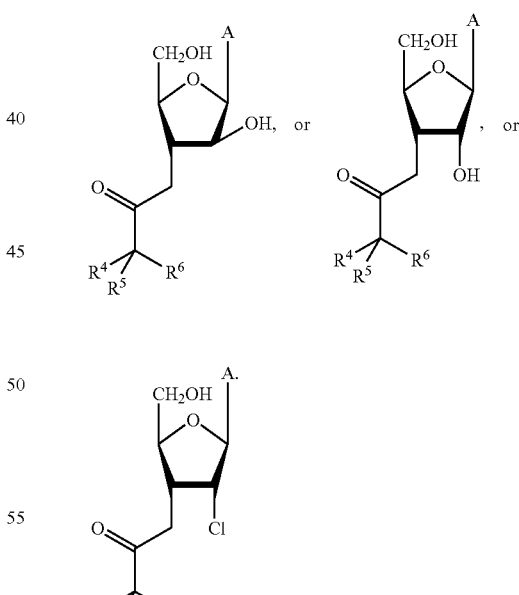

The non-peptidyl unit can be derived from (S) or (R) amino acids or peptides comprising two or more (S) or (R) amino acids or mixtures thereof.

In one specific, example, the disclosed metabolically stable nucleosides can have the formula:

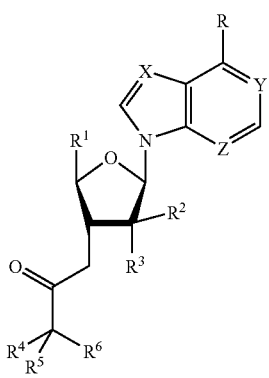

wherein X, Y, and Z are each independently chosen from CH or N.

The disclosed compounds include (6-substituted)-purin-9-yl, (4-substituted)-pyrrolo[2,3-d]pyriminid-7-yl, (7-substituted)-imidazo[4,5-b]pyridine-3-yl, (4-substituted)-benzo[d]imidazol-1-yl, (4-substituted)-pyrolo[3,2-c]pyridine-1-yl, and (4-substituted)-indol-1-yl nucleosides having the formula:

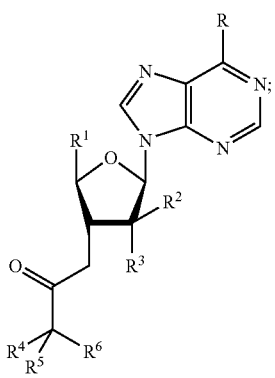

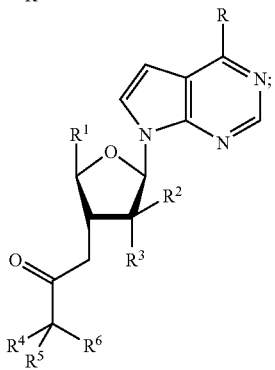

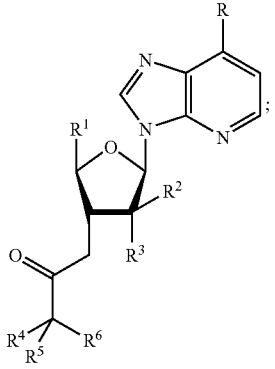

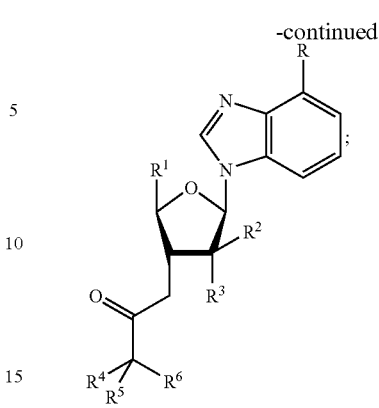

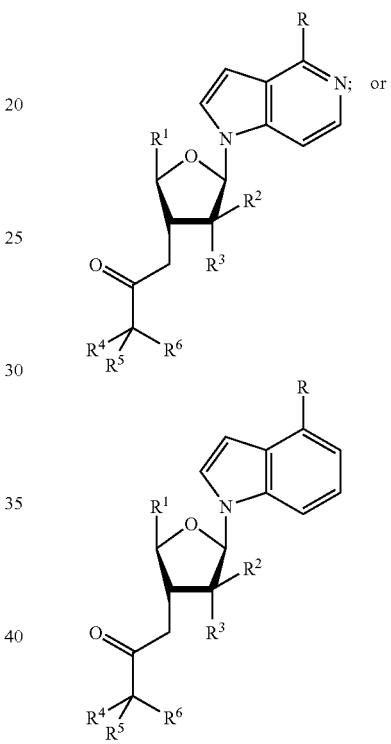

R Units

One embodiment of R units relates to compounds wherein R is hydrogen. Another embodiment encompasses R units that are chosen from substituted or unsubstituted $C_1$-$C_{12}$ linear, branched, or cyclic alkyl, alkenyl, or alkynyl. Non-limiting examples of substituted and unsubstituted linear, branched, or cyclic alkyl units include: methyl ($C_1$), aminomethyl ($C_1$), fluoromethyl ($C_1$), difluoromethyl ($C_1$), trifluoromethyl ($C_1$), ethyl ($C_2$), 1-chloroethyl ($C_2$), 2-hydroxyethyl ($C_2$), 1,2-difluoroethyl ($C_2$), n-propyl ($C_3$), iso-propyl ($C_3$), cyclopropyl ($C_3$), 2,2,2-trifluoroethyl ($C_3$), 3-carboxypropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), cyclopentyl ($C_5$), cyclohexyl ($C_6$), and the like. Non-limiting examples of substituted and unsubstituted linear, branched, or cyclic alkenyl units include: ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like. Non-limiting examples of substituted and unsubstituted linear or branched alkenyl units include: ethynyl ($C_2$), prop-2-ynyl (also propargyl) ($C_3$), propyn-1-yl ($C_3$), and 2-methyl-hex-4-yn-1-yl ($C_7$), 5-hydroxy-5-methylhex-3-ynyl ($C_7$), 6-hydroxy-6-methylhept-3-yn-2-yl ($C_9$), 5-hydroxy-5-ethylhept-3-ynyl ($C_9$), and the like.

A further embodiment of R has the formula $[C(R^{9a})(R^{9b})]_x OR^{10}$, wherein $R^{10}$ is chosen from hydrogen; for example, R units chosen from hydroxyl; hydroxymethyl ($C_1$), hydroxyethyl ($C_1$), hydroxypropyl ($C_1$), and the like; substituted or unsubstituted $C_1$-$C_{12}$ linear, branched, or cyclic alkyl; for example, R units chosen from methoxymethyl ($C_1$), methoxyethyl ($C_2$), methoxypropyl ($C_3$), methoxy-butyl ($C_4$), ethoxymethyl ($C_1$), fluoromethoxymethyl ($C_1$), difluoromethoxymethyl ($C_1$), trifluoromethoxymethyl ($C_1$), ethoxyethyl ($C_2$), ethoxypropyl ($C_3$), ethoxybutyl ($C_4$), ethoxyethyl ($C_2$), trifluoromethoxyethyl ($C_2$), and the like.

A further embodiment of R has the formula $-[C(R^{9a})(R^{9b})]_x OC(O)R^{11}$, wherein $R^{11}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl. $R^{9a}$ and $R^{9b}$ are each independently hydrogen or substituted or unsubstituted $C_1$-$C_4$ linear or branched alkyl; and the index x is from 0 to 10. $R^{9a}$, $R^{9b}$, and the index x are used throughout the specification to define alkylene tethers and have the same meaning herein below in all occurrences.

Non-limiting examples of R units include $-OC(O)CH_3$; $-OC(O)CH_2CH_3$; $-OC(O)CH_2CH_2CH_3$; $-CH_2OC(O)CH_3$; $-CH_2OC(O)CH_2CH_3$; $-CH_2OC(O)CH_2CH_2CH_3$; $-CH_2OC(O)CH(CH_3)_2$; $-OC(O)C_6H_5$; $-OC(O)CH_2C_6H_5$; $-CH_2OC(O)C_6H_5$; and $-CH_2OC(O)CH_2C_6H_5$.

A yet further embodiment of R units are halogen; fluoro (—F), chloro (—Cl), bromo (—Br), iodo (—I).

Another embodiment of R is a unit having the formula $-[C(R^{9a})(R^{9b})]_x CN$; for example, R units having the formula: —CN, —$CH_2CN$, —$CH_2CH_2CN$, and —$CH_2CH_2CH_2CN$.

A yet further embodiment of R is a unit having the formula $-[C(R^{9a})(R^{9b})]_x NO_2$; for example, R units having the formula: —$NO_2$, —$CH_2NO_2$, —$CH_2CH_2NO_2$, and —$CH_2CH_2CH_2NO_2$.

Another embodiment of R includes amino or aminoalkylene units having the formula $-[C(R^{9a})(R^{9b})]_x N(R^{12a})(R^{12b})$, wherein $R^{12a}$ and $R^{12b}$ are each independently chosen from hydrogen; substituted or unsubstituted $C_1$-$C_6$ linear, branched, or cyclic alkyl; or $R^{12a}$ and $R^{12b}$ can be taken together to form a substituted or unsubstituted ring having from 3 to 7 atoms.

Non-limiting examples of R units that are amino units include:

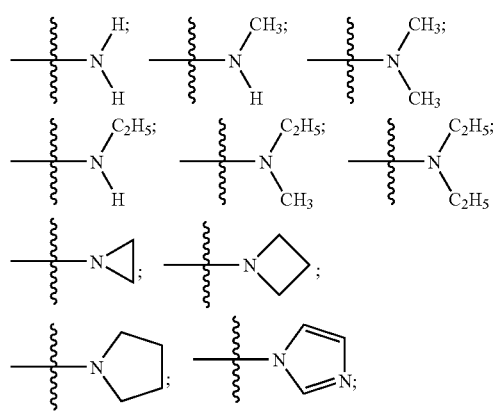

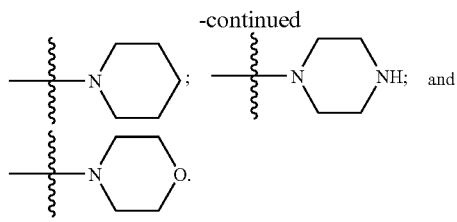

Non-limiting examples of this embodiment of R units includes (6-substituted)-purin-9-yl peptidyl nucleosides comprising an amino or substituted amino unit, for example, compounds having the formulae:

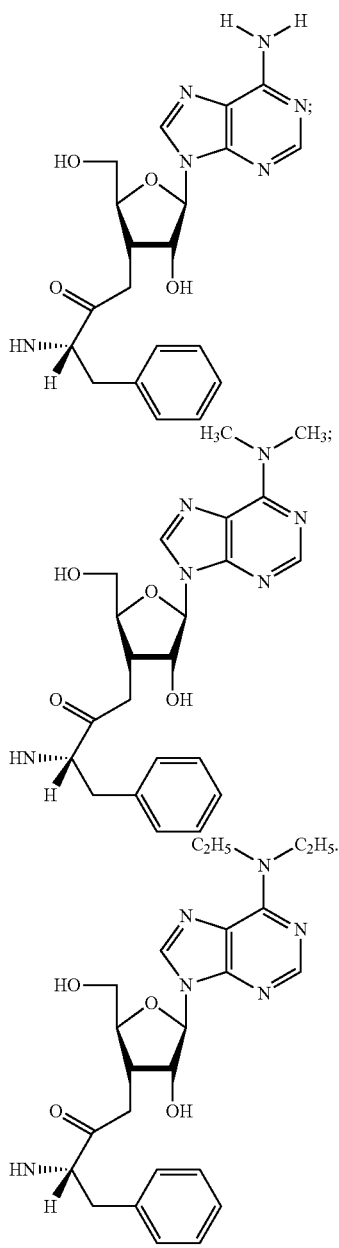

A yet further embodiment of R includes units having the formula $-[C(R^{9a})(R^{9b})]_x NR^{14}(=R^{15})R^{13}$, wherein $R^{13}$ is chosen from substituted or unsubstituted $C_1$-$C_4$ linear, branched, or cyclic alkyl, alkenyl, or alkynyl; substituted or unsubstituted $C_1$-$C_4$ linear, branched, or cyclic alkoxy; substituted or unsubstituted phenyl; substituted or unsubstituted benzyl; —N($R^{16a}$)($R^{16b}$), $R^{16a}$ and $R^{16b}$ are each independently hydrogen, substituted or unsubstituted $C_1$-$C_3$ linear alkyl, —CN, or —NO$_2$; $R^{14}$ is hydrogen or substituted or unsubstituted $C_1$-$C_4$ linear, branched, or cyclic alkyl; $R^{15}$ is O or NR$^{17}$, $R^{17}$ is hydrogen, substituted or unsubstituted $C_1$-$C_3$ linear alkyl, —OH, —CN, or —NO$_2$.

Non-limiting examples of this embodiment include —NHC(=O)NH$_2$; —NHC(=NH)NH$_2$; —NHC(=NH)NHCN; —NHC(=NH)NHNO$_2$; —NHC(=NCN)NH$_2$; —NHC(=NH)CH$_3$; —NHC(=O)CH$_3$; —NCH$_3$(=O)NH$_2$; —NCH$_3$(=NH)NH$_2$; —NCH$_3$(=NH)NHCN; —NCH$_3$(=NH)NHNO$_2$; —NCH$_3$(=NCN)NH$_2$; —NCH$_3$(=NH)CH$_3$; —NCH$_3$(=O)CH$_3$; —CH$_2$NHC(=O)NH$_2$; —CH$_2$NHC(=NH)NH$_2$; —CH$_2$NHC(=NH)NHCN; —CH$_2$NHC(=NH)NHNO$_2$; —CH$_2$NHC(=NCN)NH$_2$; —CH$_2$NHC(=NH)CH$_3$; —CH$_2$NHC(=O)CH$_3$; —CH$_2$NCH$_3$(=O)NH$_2$; —CH$_2$NCH$_3$(=NH)NH$_2$; —CH$_2$NCH$_3$(=NH)NHCN; —CH$_2$NCH$_3$(=NH)NHNO$_2$; —CH$_2$NCH$_3$(=NCN)NH$_2$; —CH$_2$NCH$_3$(=NH)CH$_3$; and —CH$_2$NCH$_3$(=O)CH$_3$.

Another embodiment of R includes units having the formula —[C($R^{9a}$)($R^{9b}$)]$_x$C(O)$R^{18}$, wherein $R^{18}$ is chosen from substituted or unsubstituted $C_1$-$C_4$ linear, branched, or cyclic alkyl, alkenyl, or alkynyl; substituted or unsubstituted $C_1$-$C_4$ linear, branched, or cyclic alkoxy; substituted or unsubstituted phenyl; substituted or unsubstituted benzyl; or —OH.

Non-limiting examples of R units include —CO$_2$H; —CO$_2$CH$_3$; —CO$_2$CH$_2$CH$_3$; —CO$_2$C$_6$H$_6$; —CO$_2$CH$_2$C$_6$H$_6$; —CH$_2$CO$_2$H; —CH$_2$CO$_2$CH$_3$; —CH$_2$CO$_2$CH$_2$CH$_3$; —CH$_2$CO$_2$C$_6$H$_6$; —CH$_2$CO$_2$CH$_2$C$_6$H$_6$; —COCH$_3$; —COCH$_2$CH$_3$; —COC$_6$H$_6$; —COCH$_2$C$_6$H$_6$; —CH$_2$COCH$_3$; —CH$_2$COCH$_2$CH$_3$; —CH$_2$COC$_6$H$_6$; and —CH$_2$COCH$_2$C$_6$H$_6$.

A further embodiment of R includes units having the formula [C($R^{9a}$)($R^{9b}$)]$_x$C(O)NR$^{19a}$R$^{19b}$, wherein R$^{19a}$ and R$^{19b}$ are each independently chosen from hydrogen; substituted or unsubstituted $C_1$-$C_6$ linear, branched, or cyclic alkyl; or R$^{19a}$ and R$^{19b}$ can be taken together to form a substituted or unsubstituted ring having from 3 to 7 atoms.

Non-limiting examples of R units include —C(O)NH$_2$; —C(O)NHCH$_3$; —C(O)NHCH$_2$CH$_3$; —C(O)NHCH$_2$CH$_2$CH$_3$; —C(O)N(CH$_3$)$_2$; —C(O)N(CH$_2$CH$_3$)$_2$; —C(O)N(CH$_3$)(CH$_2$CH$_3$); —C(O)NHC$_6$H$_5$; —C(O)NHCH$_2$C$_6$H$_5$; —CH$_2$C(O)NH$_2$; —CH$_2$C(O)NHCH$_3$; —CH$_2$C(O)NHCH$_2$CH$_3$; —CH$_2$C(O)NHCH$_2$CH$_2$CH$_3$; —CH$_2$C(O)N(CH$_3$)$_2$; —CH$_2$C(O)N(CH$_2$CH$_3$)$_2$; —CH$_2$C(O)N(CH$_3$)(CH$_2$CH$_3$); —CH$_2$C(O)NHC$_6$H$_5$; and —CH$_2$C(O)NHCH$_2$C$_6$H$_5$.

One embodiment of $R^1$ units relates to disclosed compounds wherein $R^1$ is hydrogen. Another embodiment of $R^1$ encompasses $R^1$ units that are chosen from substituted or unsubstituted $C_1$-$C_{12}$ linear, branched, or cyclic alkyl, alkenyl, or alkynyl. Non-limiting examples of substituted and unsubstituted linear, branched, or cyclic alkyl units include: methyl ($C_1$), aminomethyl ($C_1$), fluoromethyl ($C_1$), difluoromethyl ($C_1$), trifluoromethyl ($C_1$), ethyl ($C_2$), 1-chloroethyl ($C_2$), 2-hydroxyethyl ($C_2$), 1,2-difluoroethyl ($C_2$), n-propyl ($C_3$), iso-propyl ($C_3$), cyclopropyl ($C_3$), 2,2,2-trifluoroethyl ($C_3$), 3-carboxypropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), cyclo-pentyl ($C_5$), cyclohexyl ($C_6$), and the like. Non-limiting examples of substituted and unsubstituted linear, branched, or cyclic alkenyl units include: ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like. Non-limiting examples of substituted and unsubstituted linear or branched alkenyl units include: ethynyl ($C_2$), prop-2-ynyl (also propargyl) ($C_3$), propyn-1-yl ($C_3$), and 2-methyl-hex-4-yn-1-yl ($C_7$), 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

A further embodiment of $R^1$ includes units having the formula [C($R^{9a}$)($R^{9b}$)]$_x$OR$^{20}$, wherein $R^{20}$ is chosen from hydrogen; for example, $R^1$ is hydroxyl; hydroxymethyl ($C_1$), hydroxyethyl ($C_1$), hydroxypropyl ($C_1$), and the like; substituted or unsubstituted $C_1$-$C_{12}$ linear, branched, or cyclic alkyl; for example, $R^1$ is methoxymethyl ($C_1$), methoxyethyl ($C_2$), methoxypropyl ($C_3$), methoxy-butyl ($C_4$), ethoxymethyl ($C_1$), fluoromethoxymethyl ($C_1$), difluoromethoxymethyl ($C_1$), trifluoromethoxymethyl ($C_1$), ethoxyethyl ($C_2$), ethoxypropyl ($C_3$), ethoxybutyl ($C_4$), ethoxyethyl ($C_2$), trifluoro-methoxyethyl ($C_2$), and the like.

A further embodiment of $R^1$ includes units having the formula —[C($R^{9a}$)($R^{9b}$)]$_x$OC(O)R$^{21}$, wherein R$^{21}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl. Non-limiting examples of $R^1$ units include —OC(O)CH$_3$; —OC(O)CH$_2$CH$_3$; —OC(O)CH$_2$CH$_2$CH$_3$; —CH$_2$OC(O)CH$_3$; —CH$_2$OC(O)CH$_2$CH$_3$; —CH$_2$OC(O)CH$_2$CH$_2$CH$_3$; —CH$_2$OC(O)CH(CH$_3$)$_2$; —OC(O)C$_6$H$_5$; —OC(O)CH$_2$C$_6$H$_5$; —CH$_2$OC(O)C$_6$H$_5$; and —CH$_2$OC(O)CH$_2$C$_6$H$_5$.

Another embodiment of $R^1$ includes units having the formula —[C($R^{9a}$)($R^{9b}$)]$_x$C(O)R$^{22}$, wherein R$^{22}$ is chosen from substituted or unsubstituted $C_1$-$C_4$ linear, branched, or cyclic alkyl, alkenyl, or alkynyl; substituted or unsubstituted $C_1$-$C_4$ linear, branched, or cyclic alkoxy; substituted or unsubstituted phenyl; substituted or unsubstituted benzyl; or —OH. Non-limiting examples of $R^1$ units include —CO$_2$H; —CO$_2$CH$_3$; —CO$_2$CH$_2$CH$_3$; —CO$_2$C$_6$H$_6$; —CO$_2$CH$_2$C$_6$H$_6$; —CH$_2$CO$_2$H; —CH$_2$CO$_2$CH$_3$; —CH$_2$CO$_2$CH$_2$CH$_3$; —CH$_2$CO$_2$C$_6$H$_6$; —CH$_2$CO$_2$CH$_2$C$_6$H$_6$; —COCH$_3$; —COCH$_2$CH$_3$; —COC$_6$H$_6$; —COCH$_2$C$_6$H$_6$; —CH$_2$COCH$_3$; —CH$_2$COCH$_2$CH$_3$; —CH$_2$COC$_6$H$_6$; and —CH$_2$COCH$_2$C$_6$H$_6$.

A further embodiment of $R^1$ includes units having the formula —[C($R^{9a}$)($R^{9b}$)]$_x$C(O)NR$^{24a}$R$^{24b}$, wherein R$^{24a}$ and R$^{24b}$ are each independently chosen from hydrogen; substituted or unsubstituted $C_1$-$C_6$ linear, branched, or cyclic alkyl; or R$^{24a}$ and R$^{24b}$ can be taken together to form a substituted or unsubstituted ring having from 3 to 7 atoms. Non-limiting examples of R units include —C(O)NH$_2$; —C(O)NHCH$_3$; —C(O)NHCH$_2$CH$_3$; —C(O)NHCH$_2$CH$_2$CH$_3$; —C(O)N(CH$_3$)$_2$; —C(O)N(CH$_2$CH$_3$)$_2$; —C(O)N(CH$_3$)(CH$_2$CH$_3$); —C(O)NHC$_6$H$_5$; —C(O)NHCH$_2$C$_6$H$_5$; —CH$_2$C(O)NH$_2$; —CH$_2$C(O)NHCH$_3$; —CH$_2$C(O)NHCH$_2$CH$_3$; —CH$_2$C(O)NHCH$_2$CH$_2$CH$_3$; —CH$_2$C(O)N(CH$_3$)$_2$; —CH$_2$C(O)N(CH$_2$CH$_3$)$_2$; —CH$_2$C(O)N(CH$_3$)(CH$_2$CH$_3$); —CH$_2$C(O)NHC$_6$H$_5$; and —CH$_2$C(O)NHCH$_2$C$_6$H$_5$.

$R^2$ and $R^3$ are each independently chosen from hydrogen; —OH; and halogen.

$R^4$ has the formula:

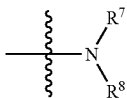

wherein $R^7$ and $R^8$ are each independently chosen from hydrogen; or —[C($R^{9a}$)($R^{9b}$)]$_x$C(O)$R^{30}$; wherein $R^{30}$ is chosen from substituted or unsubstituted $C_1$-$C_{12}$ linear, branched, or cyclic alkyl, alkenyl, or alkynyl; —O$R^{31}$; $R^{31}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl; substituted or unsubstituted phenyl; or substituted or unsubstituted benzyl.

One example of $R^4$ units includes $R^4$ units having the formula:

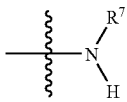

wherein $R^7$ is chosen from hydrogen or —C(O)$R^{30}$, $R^{30}$ is chosen from substituted or unsubstituted $C_1$-$C_4$ linear, branched, or cyclic alkyl; —O$R^{31}$; $R^{31}$ is chosen from substituted or unsubstituted $C_1$-$C_4$ linear or branched alkyl; or benzyl; or $R^{30}$ is substituted or unsubstituted benzyl.

Another example of $R^4$ has the formula:

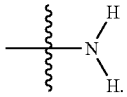

A further example of $R^4$ has the formula:

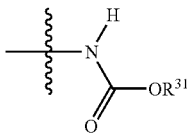

wherein $R^{31}$ is methyl ($C_1$), ethyl ($C_2$), tert-butyl ($C_4$), and benzyl ($C_7$).

A yet further example of $R^4$ is a unit having the formula:

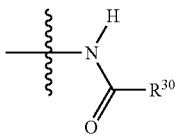

wherein $R^{30}$ is chosen from methyl ($C_1$), ethyl ($C_2$), tert-butyl ($C_4$), phenyl ($C_6$), and benzyl ($C_7$).

$R^5$ and $R^6$ are each independently chosen from hydrogen; substituted or unsubstituted $C_1$-$C_{12}$ linear, branched, or cyclic alkyl, alkenyl, or alkynyl; —[C($R^{9a}$)($R^{9b}$)]$_x$$R^{40}$; wherein $R^{40}$ is chosen from substituted or unsubstituted $C_6$ or $C_{10}$ aryl; substituted or unsubstituted $C_1$-$C_9$ heterocyclic; or substituted or unsubstituted $C_1$-$C_9$ heteroaryl; —[C($R^{9a}$)($R^{9b}$)]$_x$C($R^{42}$)$R^{41}$; wherein $R^{41}$ is chosen from hydrogen; substituted or unsubstituted $C_1$-$C_4$ linear; branched, or cyclic alkyl; —N($R^{43a}$)($R^{43b}$); wherein $R^{43a}$ and $R^{43b}$ are each independently hydrogen or substituted or unsubstituted $C_1$-$C_4$ linear or branched alkyl; —O$R^{44}$; wherein $R^{44}$ is hydrogen or substituted or unsubstituted $C_1$-$C_4$ linear or branched alkyl; and wherein $R^{42}$ is O or NH.

As described herein above, a convenient source of the non-peptidyl unit can be amino acids and peptides. When $R^5$ is hydrogen and $R^6$ is a substituted or unsubstituted $C_1$-$C_4$ alkyl, $R^6$ units can be conveniently derived from amino acids, for example —$CH_3$; alanine; —$CH(CH_3)_2$; valine; —$CH_2CH(CH_3)_2$; leucine; —$CH(CH_3)CH_2CH_3$; isoleucine; —$CH_2OH$; serine; —$CHOHCH_3$; threonine; —$CH_2SH$; cysteine; and —$CH_2SCH_3$, methionine.

$R^6$ units can also comprise substituted or unsubstituted benzyl having the formula:

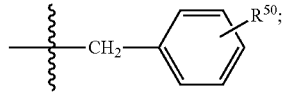

when $R^{50}$ is absent, a convenient source for $R^6$ is the amino acid phenylalanine; when $R^{50}$ is 4-hydroxy, a convenient source for $R^6$ is the amino acid tyrosine. One non-limiting example of disclosed compounds wherein $R^5$ is hydrogen and $R^6$ is substituted benzyl includes the compounds encompassed within the formula:

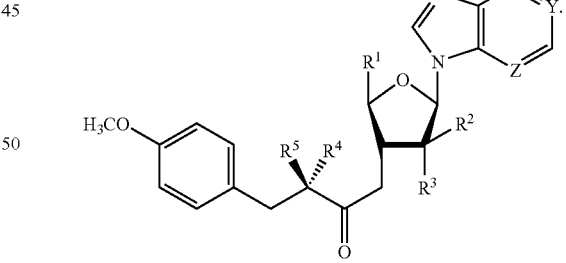

where $R^5$ and $R^6$ units further include —[$CH_2$]$_2$$R^{40}$, wherein $R^{40}$ is substituted or unsubstituted $C_3$-$C_8$ heteroaryl chosen from

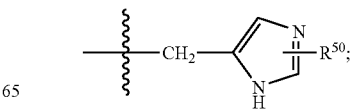

or indol-3-yl having the formula:

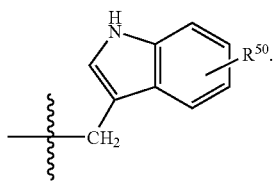

$R^5$ and $R^6$ units can also comprise units having the formula —[CH$_2$]xC(=R$^{43}$)R$^{42}$, wherein R$^{42}$ is chosen from —NH$_2$ or —OH; R$^{43}$ is O or NH; and the index x is from 0 to 4. Non-limiting examples of this embodiment includes peptidyl units wherein $R^5$ is hydrogen and a convenient source of $R^6$ are the following —CH$_2$CO$_2$H; aspartic acid;

—CH$_2$CH$_2$CO$_2$H; glutamic acid; —CH$_2$CONH$_2$; asparagine or —CH$_2$CH$_2$CONH$_2$; glutamine.

Other embodiments of $R^6$ include units having the formula —[CH$_2$]$_x$NH$_2$, wherein the index x is 2, 3, or 4. When the index x is 3 or 4, these units can be derived from the amino acids lysine and ornithine.

$R^5$ and $R^6$ also can comprise units having the formula —[CH$_2$]$_x$NHC(=R$^{47}$)R$^{46}$, wherein R$^{46}$ is —N(R$^{48a}$)(R$^{48b}$); R$^{48a}$ and R$^{48b}$ are each independently hydrogen or methyl; R$^{47}$ is O or NH; and the index x is from 0 to 4. Non-limiting examples of $R^5$ and $R^6$ units according to this embodiment include —CH$_2$NHC(NH)NH$_2$; —CH$_2$NHC(O)NH$_2$;

—CH$_2$CH$_2$NHC(NH)NH$_2$; —CH$_2$CH$_2$NHC(O)NH$_2$; —CH$_2$CH$_2$CH$_2$NHC(NH)NH$_2$; and —CH$_2$CH$_2$CH$_2$NHC(O)NH$_2$.

Synthesis

The following procedure outlined in Schemes 1-7 and described in Example 1 can be used to prepare the disclosed compounds. The following example derives the non-peptidyl unit from the amino acid (S)-phenylalanine, for example, $R^5$ is hydrogen and $R^6$ is benzyl. By substituting other N-protected amino acid esters for N-carbobenzyloxy-L-phenylalanine methyl ester, the $R^5$ and $R^6$ units can be easily varied by the formulator. However, it is not necessary to use a naturally occurring amino acid for the synthesis of the compounds disclosed herein.

Scheme 1

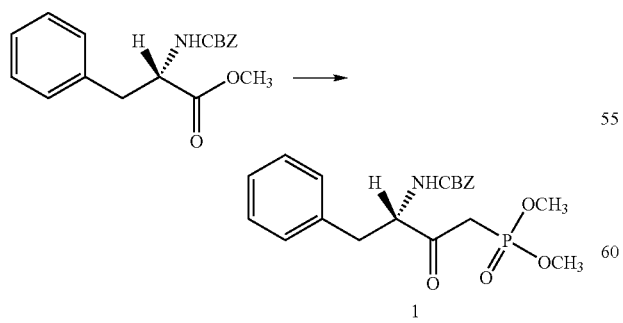

Reagents and Conditions (a): [1.6 M n-BuLi/hexanes, CH$_3$P(O)(OCH$_3$)$_2$], THF, −78° C., 1 hr, then rt, 15 min. Z is PhCH$_2$OC(O).

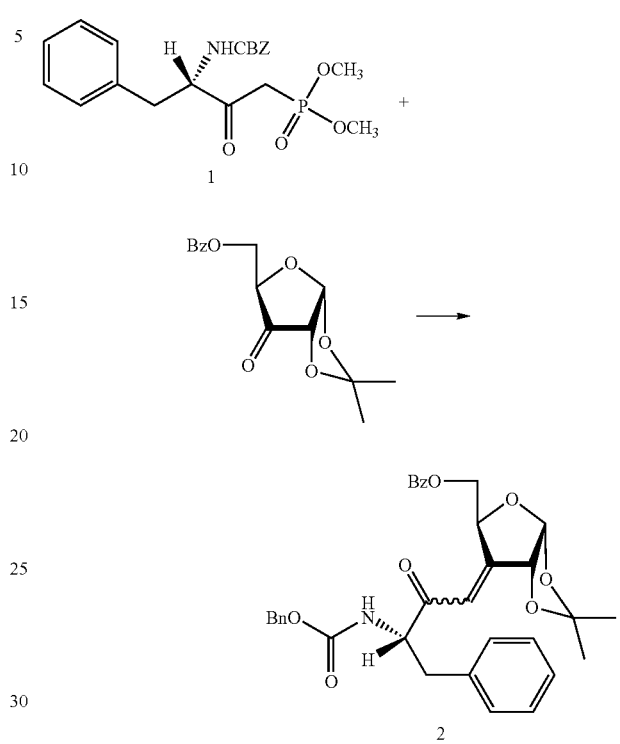

Reagents and Conditions (b): [1.6 M n-BuLi/Hexs, 5-O-benzoyl-1,2-O-isopropylidene-β-D-erythro-pentofuranos-3-ulose], THF, −78° C. (5 min) to rt, 2.5 hr.

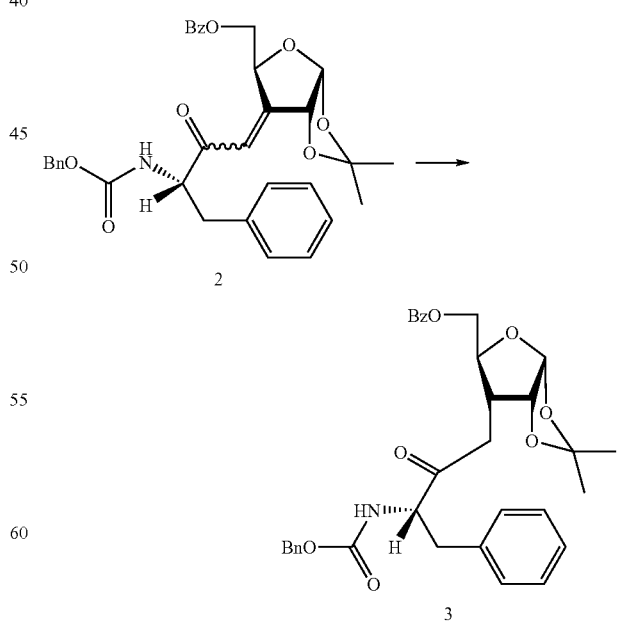

Reagents and Conditions (c): H$_2$, 10% Pd/C, acetone, 1 atm, rt, 2 hr, then PhCH$_2$OC(O)Cl, NaOH, rt, 2 hr.

Scheme 4
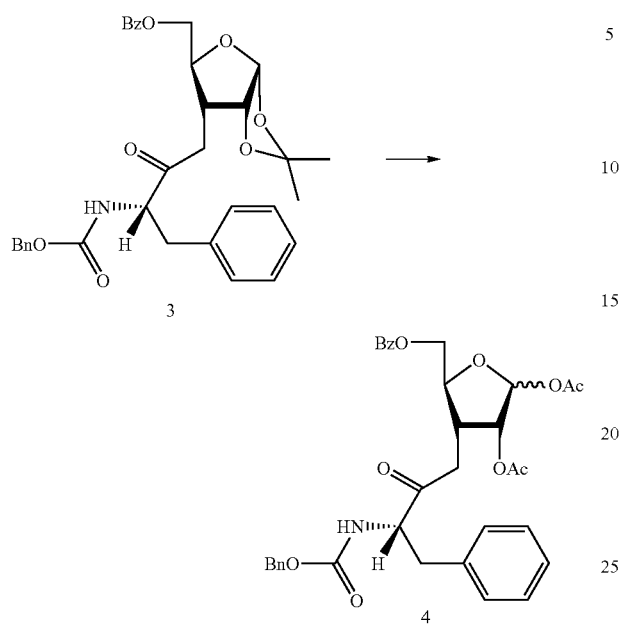
Reagents and Conditions (d): AcOH, H$_2$SO$_4$, rt, 24 hr, then Ac$_2$O, Py, rt, 24 hr.
Scheme 5
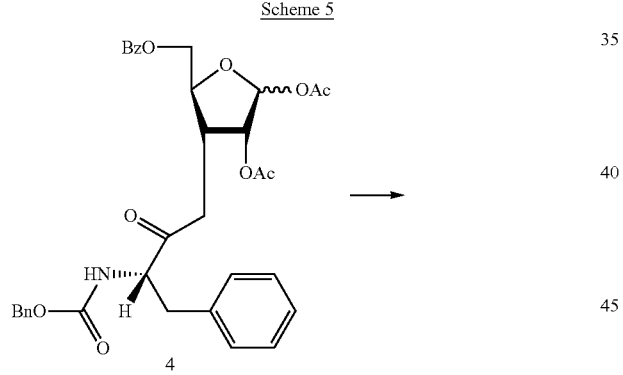
Reagents and Conditions (e): silylated 6-chloropurine, TMSOTF, MeCN, 0° C. to rt, overnight.
Scheme 6
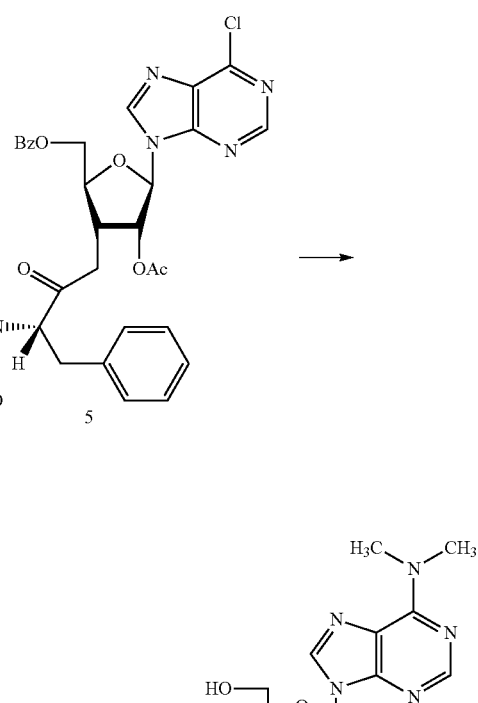
Reagents and Conditions (f): 40% MeNH$_2$/H$_2$O, MeOH, rt, 2.5 hr.
Scheme 7
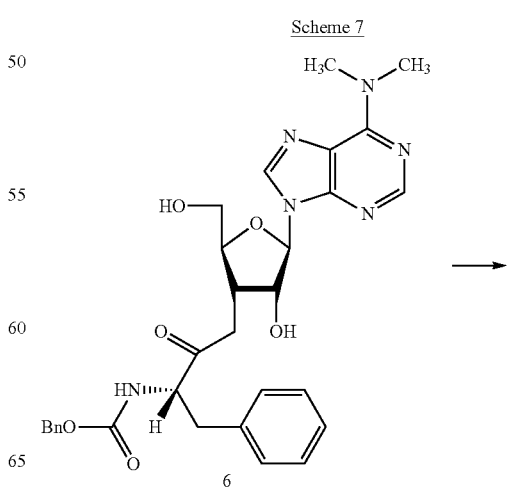

-continued

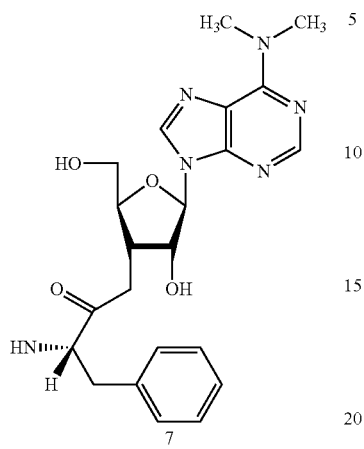

7

Reagents and Conditions (g): H$_2$, 10% Pd/C, 1 atm, rt, 6 hr.

In Scheme 1, one can use different CBZ-protected amino acid esters in order to prepare other analogs, as disclosed herein. All the 20 protected amino acids are commercially available. Reactions can be run in parallel using CAROUSEL™ and STARFISH™ reaction stations.

Intermediate 3 in Scheme 4 can also be used to produce 2'-analogs of 7, including, but not limited to, compounds 13-15, according to Schemes 8-15.

Scheme 8

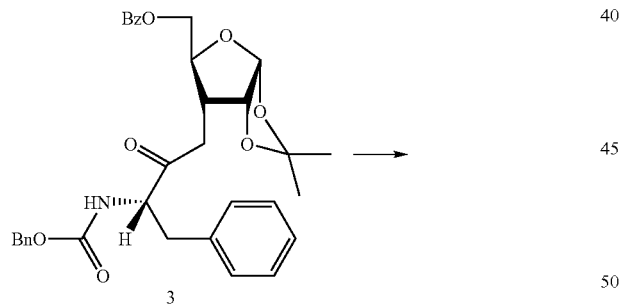

Reagents and Conditions (h): 1:2 (4.0 M HCl/dioxane)/MeOH, rt, 1.5 hr.

Scheme 9

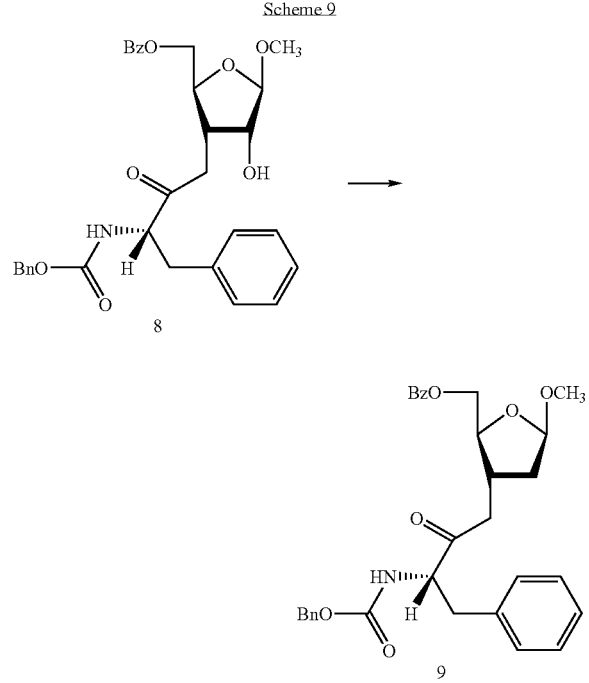

Reagents and Conditions (i): PhOC(S)Cl, DMAP, Tol, 90° C., 3 hr, then AIBN, Bu$_3$SnH, 90° C., 1 hr.

Scheme 10

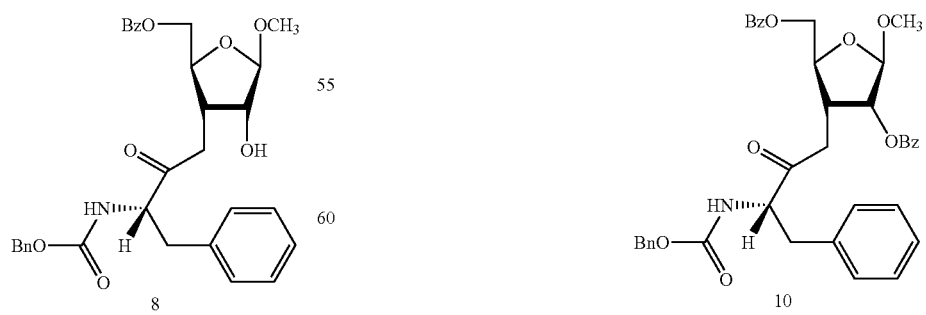

Reagents and Conditions (j): DEAD, PPh$_3$, PhCO$_2$H, THF, 0° C. to rt, 6 hr.

Scheme 11
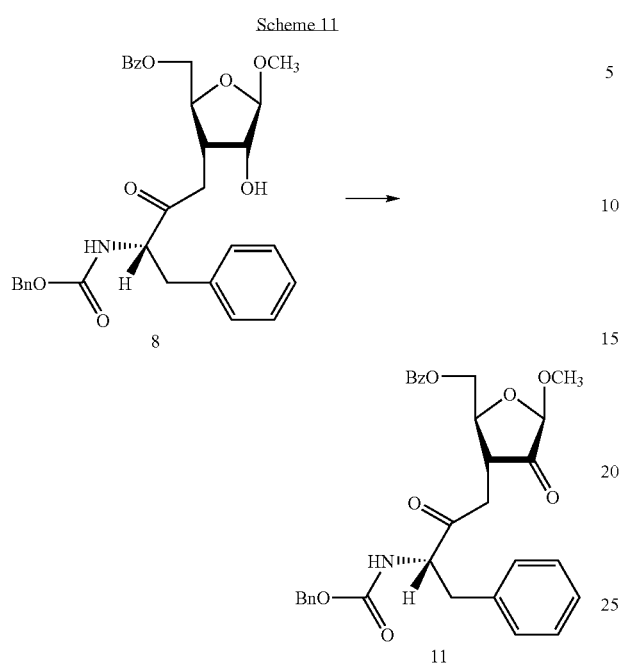
Reagents and Conditions (k): Dess-Martin reagent, CH₂Cl₂, rt, 2 hr.
Scheme 12
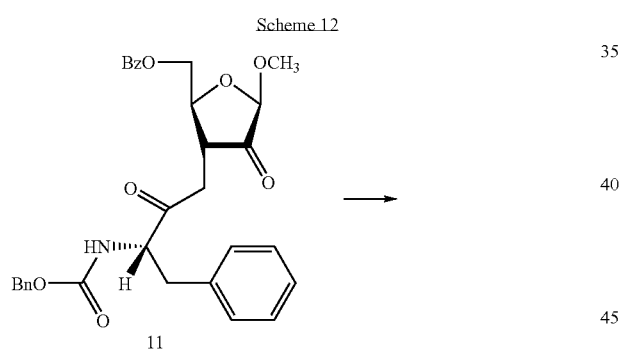
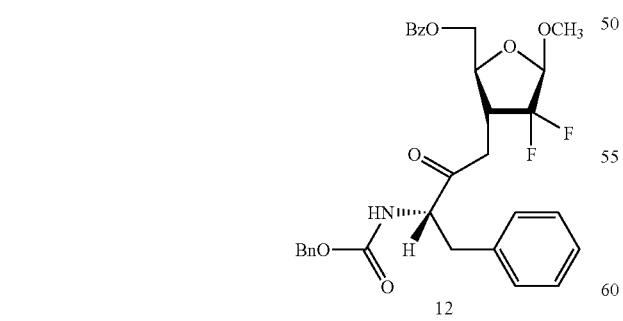
Reagents and Conditions (l): DAST, CH₂Cl₂, rt to reflux, 36 hr.
Scheme 13
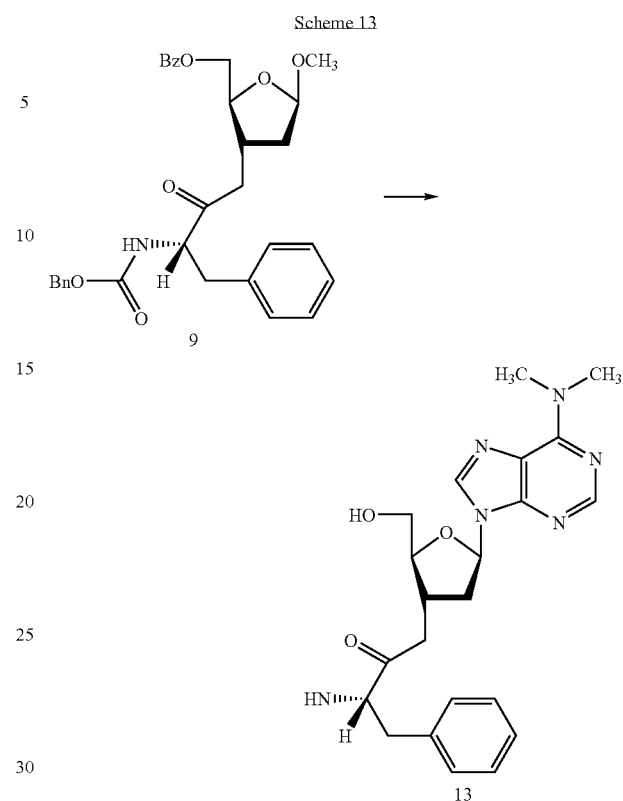
Reagents and Conditions: (d-g), Scheme 4-7.
Scheme 14
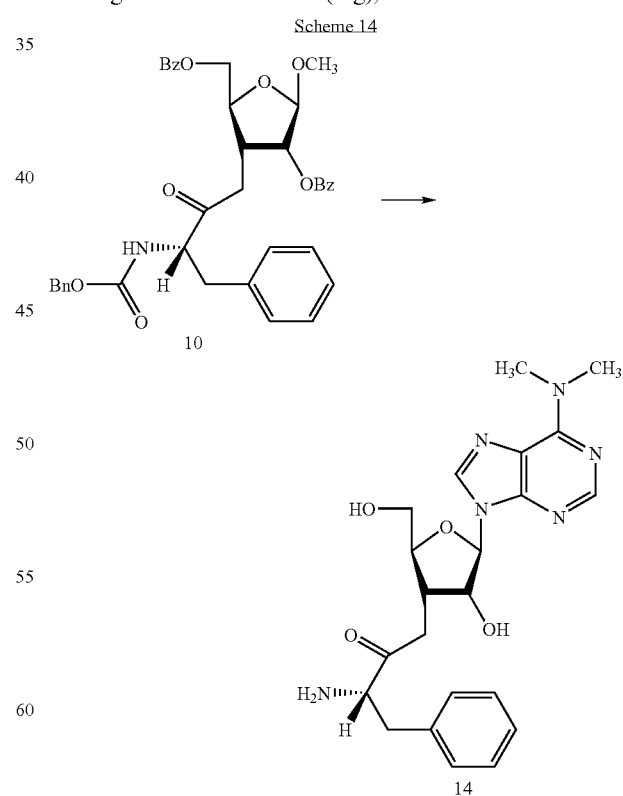
Reagents and Conditions: (d-g), Scheme 4-7.

Scheme 15

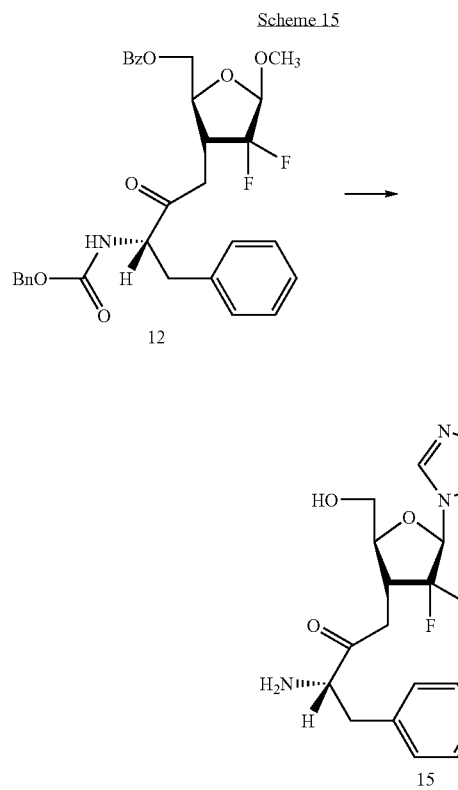

Reagents and Conditions: (d-g), Scheme 4-7.

Intermediate 3 in Scheme 4 can also be used to produce 5'-deoxy and 2',5'-dideoxy analogs of 7, including, but not limited to, compounds 20 and 21, according to Schemes 16-21.

Scheme 16

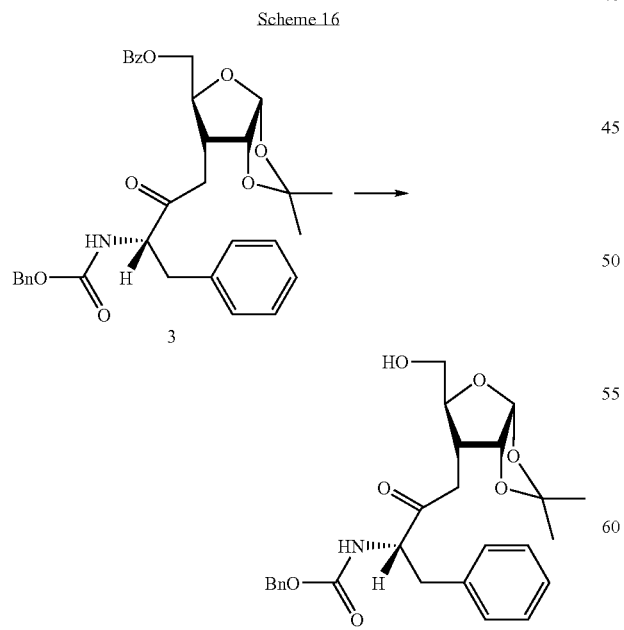

Reagents and Conditions (m): NH₃, MeOH, rt, 2 hr.

Scheme 17

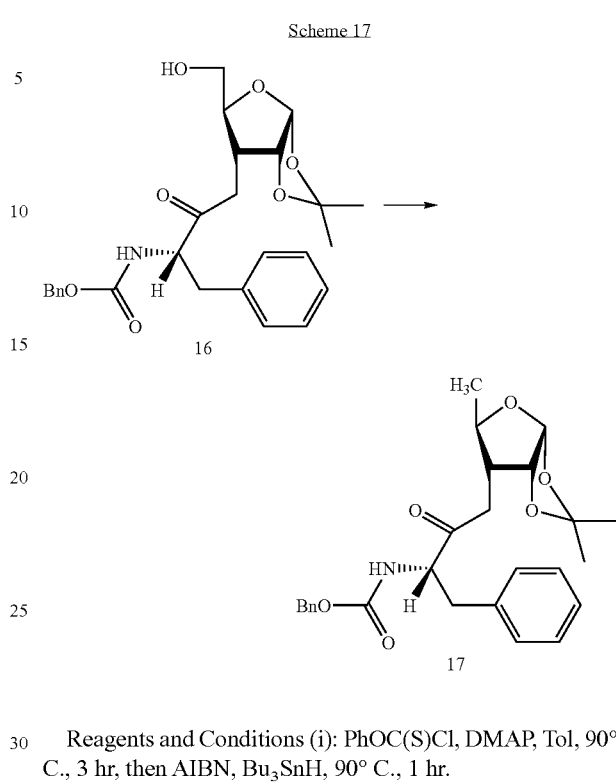

Reagents and Conditions (i): PhOC(S)Cl, DMAP, Tol, 90° C., 3 hr, then AIBN, Bu₃SnH, 90° C., 1 hr.

Scheme 18

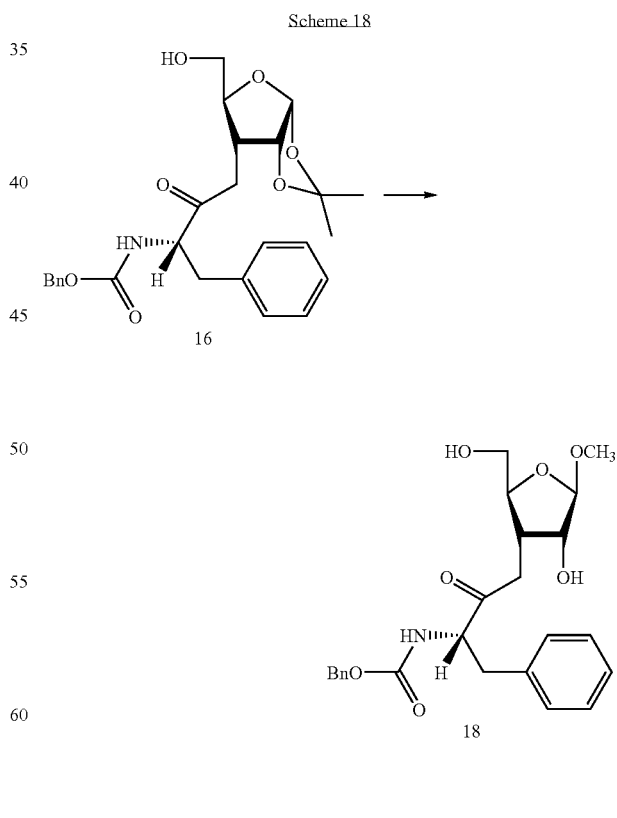

Reagents and Conditions (h): 1:2 (4.0 M HCl/dioxane)/MeOH, rt, 1.5 hr.

Scheme 19

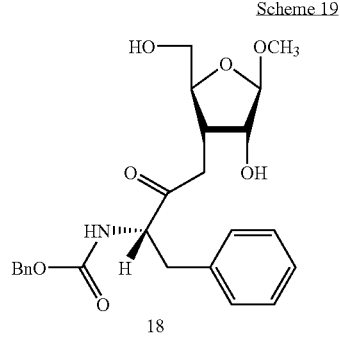

Reagents and Conditions (i): PhOC(S)Cl, DMAP, Tol, 90° C., 3 hr, then AIBN, Bu₃SnH, 90° C., 1 hr.

Scheme 20

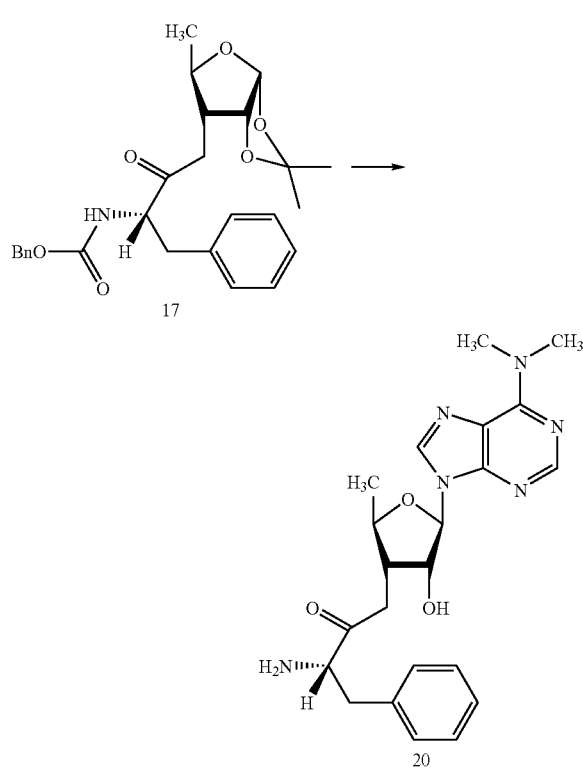

Reagents and Conditions (d-g), Scheme 4-7.

Scheme 21

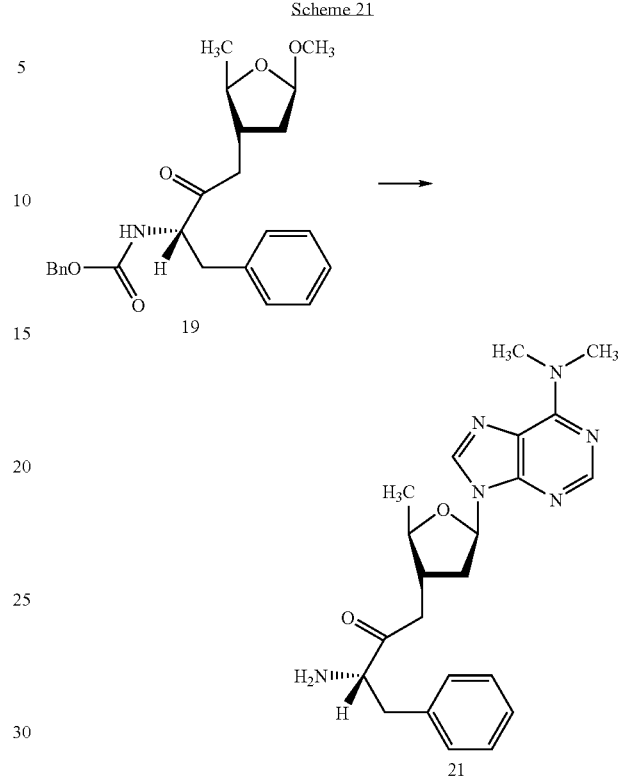

Reagents and Conditions (d-g), Scheme 4-7.

Formulations

Also, pharmaceutical formulations comprising the disclosed compounds are disclosed herein. A suitable pharmaceutical formulation can comprise any of the disclosed compositions with a pharmaceutically acceptable carrier. For example, a pharmaceutical formulation can comprise one or more of the disclosed compounds and a pharmaceutically acceptable carrier. The disclosed pharmaceutical formulations can be used therapeutically or prophylactically.

By "pharmaceutically acceptable" is meant a material that is not biologically or otherwise undesirable, i.e., the material can be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy,* 21st ed., Lippincott Williams & Wilkins, Philidelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like can be desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids, or binders can be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

When used in the above described methods or other treatments, or pharmaceutical formulations, disclosed herein, an "effective amount" of one of the disclosed microcapsules can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in the event of any counter indications. Dosage can vary, and can be administered in one or more dose administrations daily, for one or several days. Guidance can be found in the literature for appropriate dosages for given classes of pharmaceutical products. Although particular dosage regimes may be described in examples herein, a person skilled in the art would appreciated that the dosage regime may be altered to provide optimum therapeutic response. For example, several divided doses can be administered daily or the dose can be proportionally reduced as indicated by the exigencies of the therapeutic situation. In addition, the compositions of the present disclosure can be administered as frequently as necessary to achieve a therapeutic amount.

Further, disclosed are methods for delivering a disclosed composition to a subject by administering to the subject any of the pharmaceutical formulations disclosed herein.

Non-limiting examples of disclosed compositions include:
a) from about 0.001 mg to about 1000 mg of one or more modified nucleosides disclosed herein; and
b) one or more excipients.

Another embodiment of disclosed compositions includes:
a) from about 0.01 mg to about 100 mg of one or more modified peptidyl nucleosides according to the present disclosure; and
b) one or more excipients.

A further embodiment of disclosed compositions includes:
a) from about 0.1 mg to about 10 mg of one or more modified peptidyl nucleosides according to the present disclosure; and
b) one or more excipients.

Methods of Use

The present disclosure relates to methods for regulating tumor growth and thereby providing methods for treating cancer, for example, breast cancer and leukemia in a human, the method comprising administering to a human one or more of the disclosed compounds.

One embodiment of the disclosed methods relates to a method for treating breast cancer comprising administering to a human one or more of the disclosed compounds.

A further embodiment of the disclosed methods relates to a method for treating leukemia comprising administering to a human one or more of the disclosed compounds.

A yet further embodiment of the disclosed methods relates to a method for controlling tumor growth in a human or mammal comprising administering to a human or mammal having a tumor one or more of the disclosed compounds.

A further embodiment relates to a method to kill, or slow the growth of, microorganisms.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g. component concentrations, temperatures, pressures, and other reaction ranges and conditions that can be used to optimize the product purity and yield obtained from the described process. Only reasonable and routine experimentation will be required to optimize such process conditions.

Example 1

9-{3-[1-(3-Amino-2-oxo-4-phenyl)butyl]-3-deoxy-D-ribofuranosyl}-6-dimethylaminopurine (7)

Referring to Schemes 1-7 above.

Preparation of dimethyl (3S)-3-[(benzyloxycarbonyl)amino-2-oxo-4-phenylbutyl]phosphonate (1)

A 1.6 M solution of n-butyl lithium in hexanes (51.0 mL, 81.60 mmol) was added to a stirring solution of dimethyl methylphosphonate (8.8 mL, 82.34 mmol) in anhydrous tetrahydrofuran (70 mL) under argon at −78° C., and the mixture was stirred at −78° C. for 20 min. A solution of Z-L-phenylalanine methyl ester (3.19 g, 10.18 mmol) in anhydrous tetrahydrofuran (50 mL) was added to the resulting white suspension at −78° C., and the mixture was stirred at −78° C. for 1 hour, then at room temperature for 15 minutes, while releasing excess butane gas. The resulting yellow solution was cooled down in ice bath and treated with 10% acetic acid solution (50 mL). The organic layer was separated and the aqueous layer was extracted once with ethyl acetate (60 mL). The combined organic extracts were washed with saturated solution of sodium bicarbonate (2×30 mL), and brine (2×30 mL), then dried over magnesium sulfate, filtered and concentrated under reduced pressure to afford 4.59 g (>100% yield) of the desired product as a yellow oil that was used in the next step without further purification. $^1$H NMR (CDCl$_3$): δ 7.37-7.21 (m, 8H), 7.17-7.15 (m, 2H), 5.71 (d, J=7.8 Hz, 1H), 5.07 (s, 2H), 4.67 (td, J=7.8, 5.8 Hz, 1H), 3.75 (d, J=4.6 Hz, 3H), 3.72 (d, J=4.6 Hz, 3H), 3.25 (dd, J=22.4, 13.9 Hz, 1H), 3.20 (dd, J=13.9, 5.8 Hz, 1H), 3.06 (dd, J=22.4, 14.0 Hz, 1H), 2.98 (dd, J=14.0, 7.8 Hz, 1H); $^{13}$C NMR (CDCl$_3$): δ 200.8 (d, $J_{C-P}$=6.9 Hz), 156.0, 136.3, 136.3, 129.4, 128.7, 128.6, 128.3, 128.1, 127.1, 67.0, 61.7, 53.3 (d, $J_{C-P}$=5.4 Hz), 53.2 (d, $J_{C-P}$=6.1 Hz), 52.4 (d, $J_{C-P}$=6.9 Hz), 39.2, (d, $J_{C-P}$=29.0), 36.9; Mass [MH]$^+$ 406, [2M+23]$^+$ 833.

5-O-Benzoyl-1,2-O-isopropylidene-β-D-erythro-pentofuranos-3-ulose used in step (b) can be prepared according to the procedures of Hollemberg, D. H. et al. Pyridinium chlorochromate for the oxidation of carbohydrates. Carbohydr. Res. (1978) 67:491-494 and Levene, P. A.; et al. Derivatives of monoacetone xylose. J. Biol. Chem. (1933) 102:317-330, both included herein by reference in their entirety.

Preparation of 5-O-benzoyl-3-[1-(3-benzyloxycarbonylamino-2-oxo-4-phenyl)butylidene]-1,2-O-isopropylidene-α-D-erythro-pentofuranos-3-ulose (2)

A 1.6 M solution of n-butyl lithium in hexanes (5.6 mL, 8.96 mmol) was added to a stirring solution of (3S)-3-[(benzyloxycarbonyl)amino-2-oxo-4-phenylbutyl]phosphonate, 1, (3.35 g, 9.02 mmol) in anhydrous tetrahydrofuran under argon at −78° C., and the resulting solution was stirred at −78° C. for 30 minutes. A solution of 5-O-benzoyl-1,2-O-isopropylidene-β-D-erythro-pentofuranos-3-ulose (2.64 g, 9.03 mmol) in anhydrous tetrahydrofuran was slowly added at −78° C., and the resulting solution was stirred at −78° C. for 5 min, then allowed to warm up to room temperature and stirred for 2.5 hour. The solution is then washed with 0.1 N solution of hydrochloric acid (40 mL), water (2×40 mL), and brine (40 mL), dried over magnesium sulfate, filtered and concentrated under reduced pressure to a crude that is purified by thin layer chromatography grade silica gel flash column chromatography (1:4 to 3:7 ethyl acetate/hexanes) to afford 2.09 g (40% yield) of the desire product as a yellow oil. Major isomer, (Z): [α]$^{23}_D$ 131.92 (c 1.16, CHCl$_3$); $^1$H NMR (CDCl$_3$): δ 8.01-7.98 (m, 2H), 7.60-7.55 (m, 1H), 7.45-7.43 (m, 2H), 7.36-7.30 (m, 5H), 7.19-7.12 (m, 3H), 7.02-7.00 (m, 2H), 6.22 (s, 1H), 5.96 (d, J=4.1 Hz, 1H), 5.55 (d, J=7.4 Hz, 1H), 5.51 (d, J=4.1 Hz, 1H), 5.10 (d, J=12.4 Hz, 1H), 5.08-5.07 (m, 1H), 5.06 (d, J=12.4 Hz, 1H), 4.78 (dd, J=13.6, 6.6 Hz, 1H), 4.41-4.33 (m, 2H), 3.04 (d, J=6.4 Hz, 2H), 1.47 (s, 3H), 1.42 (s, 3H); $^{13}$C NMR (CDCl$_3$): δ 196.4, 166.2, 155.8, 155.3, 136.4, 135.7, 136.6, 129.9, 129.5, 129.4, 128.8, 128.7, 128.7, 128.4, 128.2, 127.4, 120.7, 113.3, 105.4, 78.7, 78.4, 67.1, 65.1, 61.5, 38.2, 27.6, 27.3; Mass [M+Na]$^+$ 594, [2M+Na]$^+$ 1165. Minor isomer, (E): [α]$^{25}_D$ 73.53 (c 0.48, CHCl$_3$); $^1$H NMR (CDCl$_3$): δ 8.12-8.09 (m, 1H), 8.00-7.97 (m, 2H), 7.64-7.55 (m, 2H), 7.50-7.41 (m, 3H), 7.35-7.29 (m, 3H), 7.24-7.22 (m, 2H), 7.13-7.11 (m, 2H), 6.24 (s, 1H), 5.97 (d, J=4.1 Hz, 1H), 5.67 (d, J=4.1 Hz, 1H), 5.40 (d, J=7.2 Hz, 1H), 5.10-5.05 (m, 3H), 4.75-4.70 (m, 1H), 4.49 (dd, J=12.0, 3.8 Hz, 1H), 4.36 (dd, J=12.0, 4.9 Hz, 1H), 3.13 (dd, J=14.2, 6.3 Hz, 1H), 3.04 (dd, J=14.2, 6.2 Hz, 1H), 1.51 (s, 3H), 1.44 (s, 3H); $^{13}$C NMR (CDCl$_3$): δ 196.2, 166.3, 155.9, 155.5, 135.7, 133.8, 133.6, 130.3, 129.8, 129.6, 128.7, 128.7, 128.7, 128.6, 128.3, 128.2, 127.3, 120.5, 113.1, 105.5, 78.5, 78.4, 67.1, 65.4, 61.4, 37.5, 27.6, 27.4; Mass [M+Na]$^+$ 594, [2M+Na]$^+$ 1165.

Preparation of 5-O-benzoyl-3-[1]-(3-benzyloxycarbonylamino-2-oxo-4-phenyl)butyl-3-deoxy-1,2-O-isopropylidene-α-D-ribose (3)

A stirring mixture of 5-O-benzoyl-3-[1-(3-benzyloxycarbonylamino-2-oxo-4-phenyl)butylidene]-1,2-O-isopropylidene-α-D-erythro-pentofuranos-3-ulose, 2, (2.23 g, 3.90 mmol) and 10% palladium on carbon (0.21 g, 0.02 mmol) in acetone (60 mL) was hydrogenated at atmospheric pressure and room temperature for 2 hours, then filtered through a pad of CELITE™, washing with acetone (3×10 mL). The filtrate was treated with benzyl chloroformate (1.1 mL, 7.81 mmol), followed by 10% solution of sodium hydroxide (3.4 mL, 8.50 mmol), and the solution was stirred at room temperature for 2 hours, then acetone was evaporated under reduced pressure and the aqueous residue was partitioned between water (50 mL) and ethyl acetate (50 mL). The organic layer was separated and the aqueous layer extracted with ethyl acetate (2×50 mL). The combined organic extracts were washed with brine (20 mL), dried over magnesium sulfate, filtered and concentrated under reduced pressure to a crude that is purified by thin layer chromatography grade silica gel flash column chromatography (1:9 to 1:4 ethyl acetate/hexanes) to afford 1.59 g (71% yield) of the desired product as a soft white foam. $^1$H NMR (CDCl$_3$): δ 8.06-8.03 (m, 2H), 7.57 (t, J=7.4 Hz, 1H), 7.47-7.42 (m, 2H), 7.38-7.29 (m, 6H), 7.24-7.21 (m, 2H), 7.13-7.10 (m, 2H), 5.83 (d, J=3.7 Hz, 1H), 5.40 (d, J=7.2 Hz, 1H), 5.11 (d, J=12.3 Hz, 1H), 5.07 (d, J=12.3 Hz, 1H), 4.74 (t, J=4.0 Hz, 1H), 4.69-4.63 (m, 1H), 4.43-4.39 (m, 1H), 4.22 (dd, J=12.7, 5.1 Hz, 1H), 4.01-3.96 (m, 1H), 3.08-3.05 (m, 2H), 2.87 (dd, J=17.9, 10.1 Hz, 1H), 2.45 (dd, J=17.9, 3.1 Hz, 1H), 2.34-2.26 (m, 1H), 1.46 (s, 3H), 1.28 (s, 3H); $^{13}$C NMR (CDCl$_3$): δ 207.2, 166.6, 155.9, 136.4, 136.0, 133.4, 130.0, 129.4, 129.0, 128.8, 128.7, 128.6, 128.5, 128.3, 127.5, 111.8, 105.2, 80.7, 79.0, 67.2, 64.0, 60.8, 40.5, 38.2, 36.4, 26.9, 26.5; Mass [M+Na]$^+$ 596, [2M+Na]$^+$ 1169.

Preparation of 5-O-benzoyl-1,2-O-diacetyl-3-[1]-(3-benzyloxycarbonylamino-2-oxo-4-phenyl)butyl-3-deoxy-β-D-ribose (4)

Concentrated sulfuric acid (25 μL, 0.47 mmol) was added to a stirring solution of 5-O-benzoyl-3-[1-(3-benzyloxycarbonylamino-2-oxo-4-phenyl)butyl]-3-deoxy-1,2-O-isopropylidene-α-D-ribose, 3, in glacial acetic acid (20 mL) at room temperature, and the resulting solution was stirred at room temperature for 24 hours. Acetic anhydride (3.0 mL, 31.74 mmol) was then added at room temperature, followed by anhydrous pyridine (0.66 mL, 0.66 mL, 8.16 mmol), and the solution is stirred at room temperature for 24 hours. Volatiles were evaporated in vacuo and the residue was dissolved in dichloromethane (50 mL), washed with saturated solution of sodium bicarbonate (10 mL), water (10 mL) and brine (10 mL), then dried over magnesium sulfate, filtered and concentrated under reduced pressure to a crude that is purified by thin layer chromatography grade silica gel flash column chromatography (1:4 ethyl acetate/hexanes) to afford 0.58 g (41% yield) of the desired product (isomeric mixture) as a soft white foam. $^1$H NMR (CDCl$_3$): δ 8.09-8.05 (m, 4H), 7.61-7.55 (m, 2H), 7.48-7.43 (m, 4H), 7.37-7.24 (m, 12H), 7.19-7.11 (m, 8H), 6.41 (m, 1H), 6.10 (m, 1H), 6.08 (s, 1H), 5.31-5.23 (m, 2H), 5.11-5.00 (m, 2H), 4.57-4.40 (m, 4H), 4.30-4.07 (m, 6H), 3.10-2.66 (m, 10H), 2.15 (s, 3H), 2.03 (s, 3H), 1.97 (s, 3H), 1.96 (s, 3H); Mass [M+Na]$^+$ 640; Analysis calcd for C$_{34}$H$_{35}$NO$_{10}$: C, 66.12; H, 5.71; N, 2.27. Found C, 65.97; H, 5.81; N, 2.25.

Preparation of 9-{2-O-acetyl-5-O-benzoyl-3-[1-(3-benzyloxycarbonylamino-2-oxo-4-phenyl)butyl]-3-deoxy-D-ribofuranosyl}-6-chloropurine (5)

A mixture of 6-chloropurine (200 mg, 1.29 mmol) and ammonium sulfate (10 mg, 0.08 mmol) in 1,1,1,3,3,3-hexamethyldisilazane (30 mL) was refluxed under argon for 4 hours. The solvent was then removed in vacuo at 40° C., and a solution of 5-O-benzoyl-1,2-O-diacetyl-3-[1-(3-benzyloxycarbonylamino-2-oxo-4-phenyl)butyl]-3-deoxy-β-D-ribose, 4, (540 mg, 0.87 mmol) in anhydrous acetonitrile (30 mL) was added followed, upon cooling down to 0° C., by trimethylsilyl trifluoromethanesulfonate (0.23 mL, 1.27 mmol). The reaction was allowed to warm up to room temperature and stirred overnight, then diluted to 100 mL with dichloromethane and slowly poured into an ice-cold saturated solution of sodium bicarbonate (50 mL). The organic layer was separated and the aqueous layer was extracted with dichloromethane (50 mL). The combined organic extracts were washed with water (20 mL) and brine (20 mL), dried over magnesium sulfate, filtered and concentrated under reduced pressure to a crude that was purified by thin layer chromatography grade silica gel flash column chromatography (1:1 ethyl acetate/hexanes) to afford 340 mg (55% yield) of the desired product as a white solid. mp 52-54° C.; [α]$^{24}_D$ 21.26 (c 0.51, CHCl$_3$); UV (MeOH) λ$_{max}$ 264.5, 230.0; $^1$H NMR (CDCl$_3$): δ 8.64 (s, 1H), 8.22 (s, 1H), 7.94-7.90 (m, 2H), 7.62-7.56 (m, 1H), 7.46-7.40 (m, 2H), 7.37-7.23 (m, 8H), 7.17-7.13 (m, 2H), 5.99 (s, 1H), 5.83 (d, J=5.8 Hz, 1H), 5.27 (t, J=7.4 Hz, 1H), 5.07 (d, J=12.1 Hz, 1H), 5.04 (d, J=12.1 Hz, 1H), 4.66-4.50 (m, 2H), 4.40 (dd, J=12.6, 4.6 Hz, 1H), 4.24-4.20 (m, 1H) 3.41-3.33 (m, 1H), 3.04-3.02 (m, 2H), 2.87 (dd, J=18.5, 9.8, 1H), 2.47 (dd, J=18.5, 4.3, 1H), 2.08 (s, 3H); Mass [M+Na]$^+$ 712, [M+Na]$^+$ 734; Analysis calcd for C$_{37}$H$_{34}$ClN$_5$O$_8$: C, 62.40; H, 4.81; N, 9.83. Found C, 62.43; H, 4.99; N, 9.54.

Preparation of 9-{3-[1-(3-benzyloxycarbonylamino-2-oxo-4-phenyl)butyl]-3-deoxy-D-ribofuranosyl}-6-chloropurine (6)

A solution of 9-{2-O-acetyl-5-O-benzoyl-3-[1-(3-benzyloxycarbonylamino-2-oxo-4-phenyl)butyl]-3-deoxy-D-ribofuranosyl}-6-chloropurine, 5, (120 mg, 0.17 mmol) in methanol (2 mL) was treated with a 40% dimethylamine aqueous solution (10 mL) at rt. The resulting solution was stirred at room temperature for 2.5 hours, then volatiles were evaporated under reduced pressure, and the aqueous residue was extracted with dichloromethane (3×40 mL). The combined organic layers were washed with brine (20 mL), dried over magnesium sulfate, filtered and concentrated under reduced pressure to a crude that is purified by preparative thin layer: chromatography (1:19 methanol/dichloromethane) to afford 60 mg (62% yield) of the desired product as a white solid. $^1$H NMR (DMSO-d$_6$): δ 8.38 (s, 1H), 8.24 (s, 1H), 7.44-7.08 (m, 10H), 6.23 (s, 1H), 5.95 (m, 1H), 5.06 (t, J=5.9 Hz, 1H), 4.97-4.95 (m, 1H), 4.92 (s, 2H), 4.66-4.50 (m, 2H), 4.44-4.39 (m, 1H), 3.88-3.81 (m, 1H) 3.63-3.42 (m, 6H), 3.18-3.08 (m, 1H), 2.63-2.58 (m, 1H), 2.50-2.48 (m, 2H), 2.26-2.19 (m, 1H); Mass [M+Na]$^+$ 575.

Preparation of 9-{3-[1-(3-amino-2-oxo-4-phenyl)butyl]-3-deoxy-D-ribofuranosyl}-6-dimethylaminopurine (7)

A mixture of -{3-[1-(3-benzyloxy-carbonylamino-2-oxo-4-phenyl)butyl]-3-deoxy-D-ribofuranosyl}-6-chloropurine, 6, (100 mg, 0.17 mmol) and 10% palladium on carbon (37 mg, 0.03 mmol) in glacial acetic acid (8 mL) was hydrogenated at atmospheric pressure and room temperature for 6 hours, then filtered through a pad of CELITE™, washing with acetic acid (3×5 mL). The solvent is then removed in vacuo, and the residue is purified by thin layer chromatography grade silica gel flash column:chromatography (1:19 methanol/dichloromethane), then by preparative thin layer:chromatography (1:9 methanol/dichloromethane, extracting with 2:23 methanol/dichloromethane) to afford the desired product as a yellow solid. UV (MeOH) $\lambda_{max}$ 272.0; $^1$H NMR (DMSO-d$_6$): δ 8.48 (s, 1H), 8.22 (s, 1H), 7.38-7.12 (m, 5H), 5.99 (s, 1H), 5.75 (m, 1H), 5.18 (t, J=5.0 Hz, 1H), 4.33 (t, J=4.4 Hz, 1H) 4.09-3.98 (m, 4H), 3.65-3.42 (m, 8H), 3.21-3.17 (m, 2H), 3.11-3.04 (m, 1H), 3.00-2.91 (m, 1H), 2.83-2.78 (m, 1H); Mass [M+Na]$^+$ 441.

Example 2

Cytotoxicity Assay

Dump media and wash wells with PBS. Add approx 100 μL 10% TCA to wells using squirt bottle. Incubate at 4° C. for 30 minutes to 1 hour. Dump TCA and wash plate 5 times with water (use beaker for washes). Add 100 ul SRB dye to wells. Incubate at room temperature for 30 minutes. Dump dye and wash plate 4 times with 1% acetic acid (use beaker for washes). Add 200 μL Tris Base to wells. Incubate at room temperature with agitation for at least 1 hour. Use Softmax pro plate reader with SRB560.

Example 3

MTS Assay

HL-60 cells were plated at a density of 4,000 cells/well (99 μL/well) in a 96-well microtiter plate. The drug (dissolved in 1 μL of DMSO/medium solution) was added and cells were incubated at 37° C. for 72 h. 20 μL of a solution of MTS/PMS (Promega, 5% PMS/MTS) was then added, the cells were incubated for 1 h, after which absorbance was read at 490 nm.

Example 4

SRB Assay

MCF-7 cells were plated at a density of 50,000 cells/well (99 μL/well) in a 96-well microtiter plate and allowed to adhere at 37° C. for 4 h. The drug (dissolved in 1 μL of DMSO/medium solution) was added and cells were incubated at 37° C. for 72 h. 100 μL of a 10% solution of trichloroacetic acid was then added and the cells were incubated for 1 h at 4° C. The supernatant was removed and the plate was washed 5 times with water. 100 μL of SRB dye (Promega) was added and the plate was incubated at rt for 30 min. The dye was removed and the plate was washed 4 times with 1% acetic acid solution. 200 μL of Tris Base was added, and the plate was incubated at rt with agitation for 1 h. Absorbance was read at 560 nm.

Example 5

Antitumor Effects

Model: JC murine mammary adenocarcinoma cells growing in Balb/c mice. Treatment is started when tumor are small, typically ~20 mm3.

Treatment: Drug was administered by intraperitoneal injection on days 7, and 12 at 50 mg/kg dissolved in 50% DMSO:50% PBS.

Figure 3:
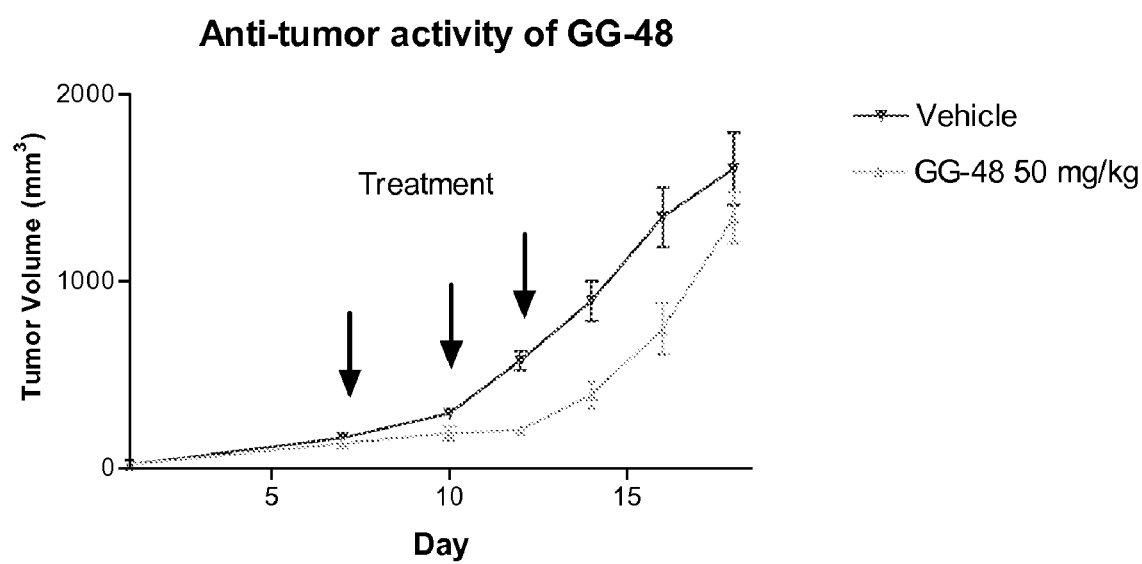
FIG. 3 is a graph of the effect of GG-48 versus puromycin on tumor growth in a murine mammary tumor model.
Figure 4:
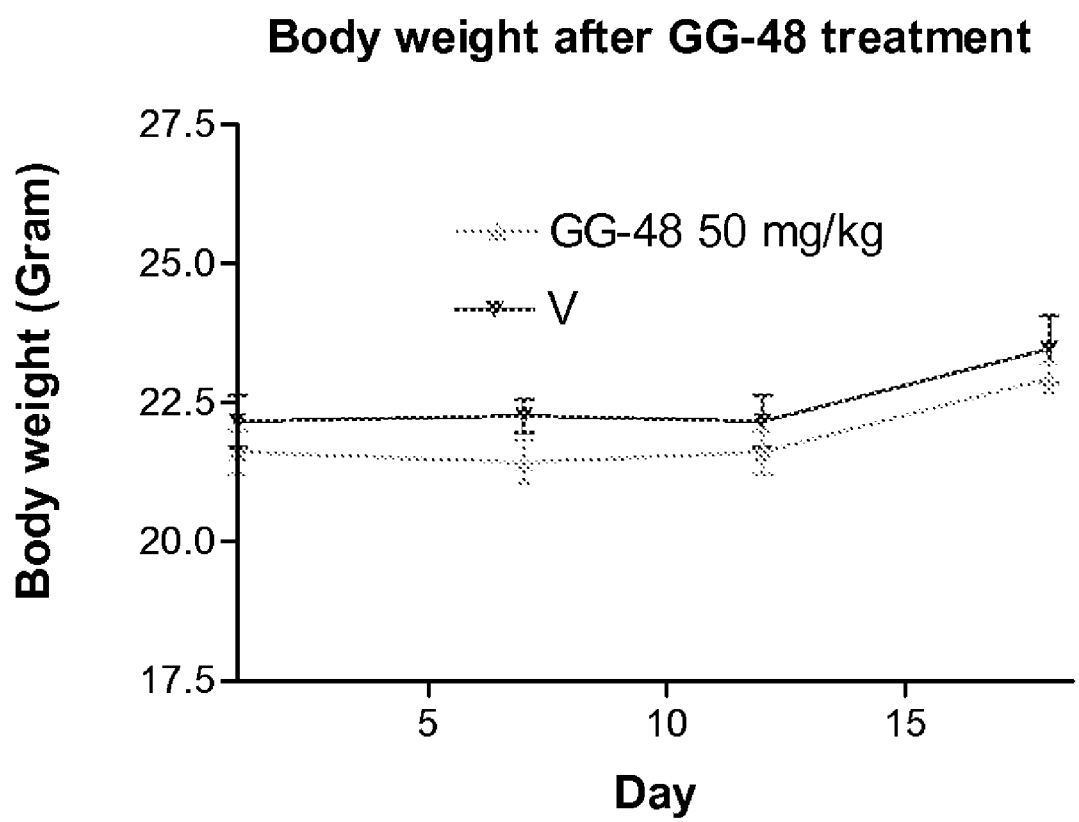
FIG. 4 is a graph of the effect of GG-48 versus puromycin on body weight in a murine mammary tumor model.

Results: GG-48 suppressed tumor growth (see FIG. 3); upon discontinuation of treatment (because of lack of drug) the tumors began to grow at the normal rate. This implies that the compound is cytostatic. There was no obvious toxicity at this dose since there was no loss of body weight during the treatment period (or after). (See FIG. 4).

Example 6

Prophetic Example of Anti-microbial Effects

Evaluation of antimicrobial activity on strains of Bacillus subtilis and cereus as model for B. anthracis and evaluation on Methicillin-resistant S. aureus will be performed. Antimicrobial effects are not limited to the strains or classifications listed. Antimicrobial evaluations will be accomplished used adaptations of methods previously used and published by (Gilbert et al. Tetrahedron, 2005, 61, 8339-8344).

Minimum Inhibitory Concentration (MIC) and Minimum Bactericidal Concentration (MBC) Tests (Prophetic Example). MIC testing is performed using Bacillus subtilis ATCC 6633 as a control strain and Bacillus cereus ATCC 10987, an organism that has been shown to be genetically similar to Bacillus anthracis. The dihydrochloride of GG-48 is dissolved in purified water and diluted in Mueller-Hinton broth supplemented with 25 mg/L of calcium and 12.5 mg/L of magnesium (CSMHB) for in vitro microbiologic testing using two-fold dilutions ranging from concentrations of 100 to 0.04 μg/mL. MIC testing is performed in triplicate for each dilution series according to guidelines of the National Committee for Clinical Laboratory Standards (NCCLS) for S. aureus. The bacterial inoculum is prepared by inoculating the organisms into separate test tubes containing 5 mL of CSMHB and incubating the suspension at 35° C. overnight until visually turbid. These actively growing cultures are photometrically matched to a 0.5 McFarland turbidity standard. The adjusted culture is diluted with CSMHB to yield a final inoculum of approximately 105-106 organisms/mL. 50 μL of sterile CSMHB is delivered into each well in sterile 96 well microdilution trays. Then, 50 μL of GG-48 is introduced into the first well of each of three rows in the tray and serially two-fold diluted in each of the remaining rows. The bacterial inoculum (50 μL) is introduced into each well so that each well in the tray contained a total volume of 100 μL. Positive (for growth of the organism) and negative (for initial sterility of the broth) controls are assessed. After inoculation, all microdilution plates are sealed and incubated at 35° C. for 18 hours. The MIC is defined as the lowest concentration of the agent that completely inhibited growth of the microorganism as detected by the unaided eye. Minimum bactericidal testing (MBC) testing is determined in duplicate by subculturing from all nonturbid wells. Using a calibrated pipet, 20 μL is subcultured in duplicate, plated onto antibiotic-free Mueller-Hinton agar plates, and incubated at 35° C. for 24 hours. The MBC is defined as the lowest antibiotic concentration that decreased the final inoculum by ≧99.9%. MIC and MBC are interpreted based on the lowest value obtained from the traditional or intermediate concentration range. Agents that kill microorganism by inhibiting protein synthesis serve the purpose of fighting protein toxin-producing microorganisms, such as B. anthracis, and C. botulinum.

Compound GG-48 is a structural analog of the natural antitumor antibiotic puromycin. GG-48 has a methylene (CH$_2$) in place of an amide NH group. The metabolic cleavage of the amide bond in puromycin generates the nephrotoxic metabolite puromycin aminonucleoside (PAN). This metabolite cannot form from GG-48, which does not contain the necessary 3'—NH functionality (see below).

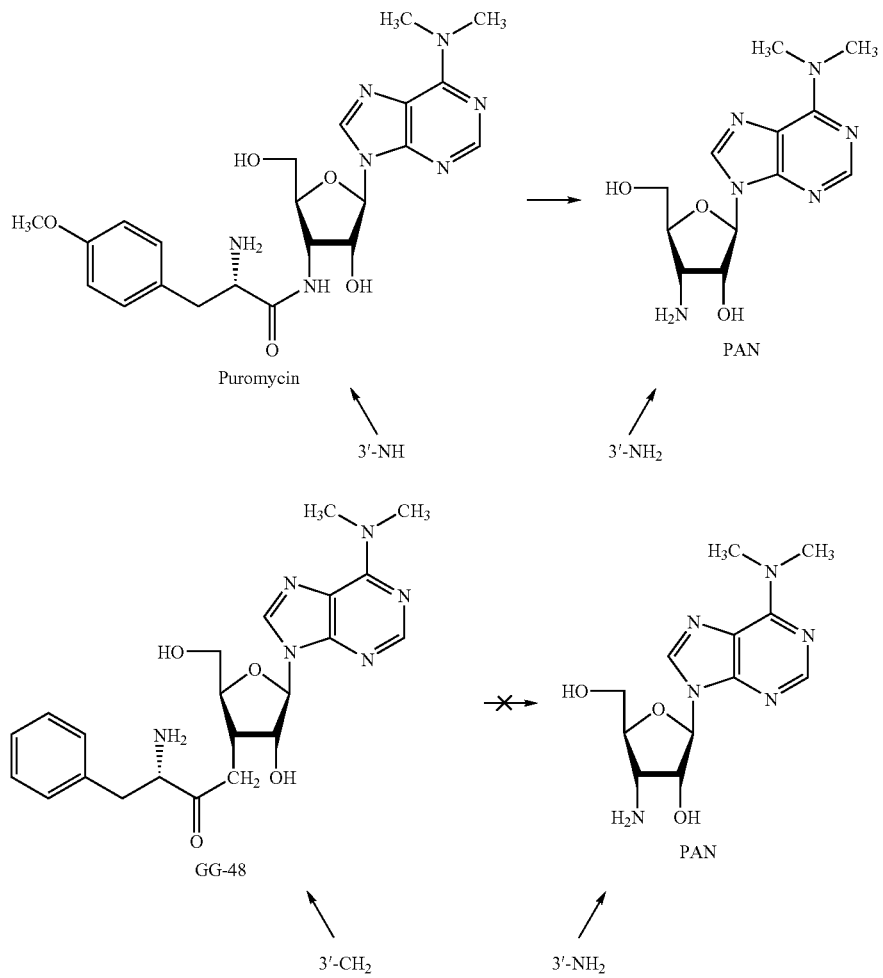

As demonstrated by the cytotoxic activity of GG-48, with killing curves overlapping those of puromycin, the replacement does not affect the activity of GG-48. The very close structural similarity of the two molecules and the almost identical cell killing profile are evidence that GG-48 acts by the same mechanism of puromycin, that is by mimicking of aminoacyl-tRNA. Both molecules would therefore serve as false substrates of the ribosome, which incorporates them into the growing proteins thereby terminating further elongation. The cell dies because of the inability of synthesizing new proteins. Since the mechanism of action that leads to the demonstrated cytotoxicity of GG-48 is the same as the mechanism for antimicrobial activity, GG-48 would show similar antimicrobial activity as puromycin, which we measured to be 3.13 μg/mL against both *B. subtilis* and *B. cereus* strains (Gilbert et al., *Tetrahedron*, 2005, 61, 8339-8344).

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A compound, or pharmaceutically acceptable salt thereof, having the formula:

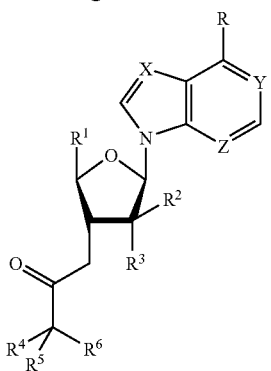

wherein X, Y, and Z are each independently chosen from CH or N;
R is a unit chosen from:
a) hydrogen;
b) $C_1$-$C_{12}$ substituted or unsubstituted linear, branched, or cyclic alkyl, alkenyl, or alkynyl;
c) —[C($R^{9a}$)($R^{9b}$)]$_x$O$R^{10}$;

$R^{10}$ is chosen from:
i) hydrogen;
ii) substituted or unsubstituted $C_1$-$C_{12}$ linear, branched, or cyclic alkyl; and
iii) —C(O)$R^{11}$; $R^{11}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl;
d) halogen;
e) —[C($R^{9a}$)($R^{9b}$)]$_x$CN;
f) —[C($R^{9a}$)($R^{9b}$)]$_x$NO$_2$;
g) —[C($R_{9a}$)($R^{9b}$)]$_x$N($R^{12a}$)($R^{12b}$);
$R^{12a}$ and $R^{12b}$ are each independently chosen from:
i) hydrogen;
ii) substituted or unsubstituted $C_1$-$C_6$ linear, branched, or cyclic alkyl; and
iii) $R^{12a}$ and $R^{12b}$ can be taken together to form a substituted or unsubstituted ring having from 3 to 7 atoms;
h) —[C($R^{9a}$)($R^{9b}$)]$_x$N$R^{14}$C(=$R^{15}$)$R^{13}$;
$R^{13}$ is chosen from:
i) substituted or unsubstituted $C_1$-$C_4$ linear, branched, or cyclic alkyl, alkenyl, or alkynyl;
substituted or unsubstituted $C_1$-$C_4$ linear, branched, or cyclic alkoxy;
iii) substituted or unsubstituted phenyl;
iv) substituted or unsubstituted benzyl; and
v) —N($R^{16a}$)($R^{16b}$), $R^{16a}$ and $R^{16b}$ are each independently hydrogen, substituted or unsubstituted $C_1$-$C_3$ linear alkyl, —CN, or —NO$_2$;
$R^{14}$ is hydrogen or substituted or unsubstituted $C_1$-$C_4$ linear, branched, or cyclic alkyl;
$R^{15}$ is O or N$R^{17}$, $R^{17}$ is hydrogen, substituted or unsubstituted $C_1$-$C_3$ linear alkyl, —OH, —CN, or —NO$_2$;
i) —[C($R^{9a}$)($R^{9b}$)]$_x$C(O)$R^{18}$; and
$R^{18}$ is chosen from:
i) substituted or unsubstituted $C_1$-$C_4$ linear, branched, or cyclic alkyl, alkenyl, or alkynyl;
ii) substituted or unsubstituted $C_1$-$C_4$ linear, branched, or cyclic alkoxy;
iii) substituted or unsubstituted phenyl;
iv) substituted or unsubstituted benzyl; and
v) —OH;
j) —[C($R^{9a}$)($R^{9b}$)]$_x$C(O)N$R^{19a}R^{19b}$;
$R^{19a}$ and $R^{19b}$ are each independently chosen from:
i) hydrogen;
ii) substituted or unsubstituted $C_1$-$C_6$ linear, branched, or cyclic alkyl; and
iii) $R^{19a}$ and $R^{19b}$ can be taken together to form a substituted or unsubstituted ring having from 3 to 7 atoms;
$R^1$ is a unit chosen from:
a) hydrogen;
b) substituted or unsubstituted $C_1$-$C_{12}$ linear, branched, or cyclic alkyl, alkenyl, or alkynyl;
c) —[C($R^{9a}$)($R^{9b}$)]$_x$O$R^{20}$;
$R^{20}$ is chosen from:
i) hydrogen;
ii) substituted or unsubstituted $C_1$-$C_{12}$ linear, branched, or cyclic alkyl; and
iii) —C(O)$R^{21}$; $R^{21}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl;
d) —[C($R^{9a}$)($R^{9b}$)]$_x$C(O)$R^{22}$; and
$R^{22}$ is chosen from:
i) substituted or unsubstituted $C_1$-$C_4$ linear, branched, or cyclic alkyl, alkenyl, or alkynyl;

ii) substituted or unsubstituted $C_1$-$C_4$ linear, branched, or cyclic alkoxy;
iii) substituted or unsubstituted phenyl;
iv) substituted or unsubstituted benzyl; and
v) —O$R^{23}$; $R^{23}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl;
e) —[C($R^{9a}$)($R^{9b}$)]$_x$C(O)N$R^{24a}R^{24b}$;
$R^{24a}$ and $R^{24b}$ are each independently chosen from:
i) hydrogen;
ii) substituted or unsubstituted $C_1$-$C_6$ linear, branched, or cyclic alkyl; and
iii) $R^{24a}$ and $R^{24b}$ can be taken together to form a substituted or unsubstituted ring having from 3 to 7 atoms;
$R^2$ and $R^3$ are each independently chosen from:
a) hydrogen;
b) —OH; and
c) halogen;
$R^4$ has the formula:

$$-\text{N}\begin{smallmatrix}R^7\\R^8\end{smallmatrix}$$

$R^7$ and $R^8$ are each independently chosen from:
a) hydrogen; or
b) —[C($R^{9a}$)($R^{9b}$)]$_x$C(O)$R^{30}$;
$R^{30}$ is chosen from:
i) substituted or unsubstituted $C_1$-$C_{12}$ linear, branched, or cyclic alkyl, alkenyl, or alkynyl;
ii) —O$R^{31}$; $R^{31}$ is chosen from hydrogen; substituted or unsubstituted $C_1$-$C_{12}$ linear, branched, or cyclic alkyl, alkenyl, or alkynyl; substituted or unsubstituted phenyl; or substituted or unsubstituted benzyl;
iii) substituted or unsubstituted phenyl; and
iv) substituted or unsubstituted benzyl;
$R^5$ and $R^6$ are each independently chosen from:
a) hydrogen;
b) substituted or unsubstituted $C_1$-$C_{12}$ linear, branched, or cyclic alkyl, alkenyl, or alkynyl;
c) —[C($R^{9a}$)($R^{9b}$)]$_x R^{40}$; and
$R^{40}$ is chosen from:
i) substituted or unsubstituted $C_6$ or $C_{10}$ aryl;
ii) substituted or unsubstituted $C_1$-$C_9$ heterocyclic; and
ii) substituted or unsubstituted $C_1$-$C_9$ heteroaryl;
d) —[C($R^{9a}$)($R^{9b}$)]$_x$($R^{42}$)$R^{41}$;
$R^{41}$ is chosen from
i) hydrogen;
ii) substituted or unsubstituted $C_1$-$C_4$ linear; branched, or cyclic alkyl;
iii) —N($R^{43a}$)($R^{43b}$); and
$R^{43a}$ and $R^{43b}$ are each independently hydrogen or substituted or unsubstituted $C_1$-$C_4$ linear or branched alkyl;
iv) —O$R^{44}$;
$R^{44}$ is hydrogen or substituted or unsubstituted $C_1$-$C_4$ linear or branched alkyl;
$R^{42}$ is O or NH;
$R^{9a}$ and $R^{9b}$ are each independently hydrogen or substituted or unsubstituted $C_1$-$C_4$ linear or branched alkyl;
the index x is from 0 to 10.

2. The compound according to claim 1, wherein X, Y, and Z are N.

3. The compound according to claim 1, wherein X is CH and Y and Z are both N.

4. The compound according to claim 1, wherein X is N and Y and Z are both CH.

5. The compound according to claim 1, wherein R is substituted or unsubstituted $C_1$-$C_{12}$ linear, branched, or cyclic alkyl, alkenyl, or alkynyl.

6. The compound according to claim 1, wherein R is halogen.

7. The compound according to claim 1, wherein R is chosen from cyano, cyanomethyl, cyanoethyl, nitro, nitromethyl, and nitroethyl.

8. The compound according to claim 1, wherein R has the formula:

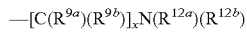

wherein $R^{12a}$ and $R^{12b}$ are each independently chosen from hydrogen, methyl, ethyl, n-propyl, and isopropyl; $R^{9a}$ and $R^{9b}$ are each independently hydrogen or methyl; the index x is from 0 to 2.

9. The compound according to claim 1, wherein R has the formula:

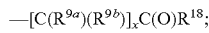

$R^{18}$ is hydrogen, hydroxy, methyl, methoxy, ethyl, ethoxy, or benzyl; $R^{9a}$ and $R^{9b}$ are each independently hydrogen or methyl; the index x is from 0 to 2.

10. The compound according to claim 1, wherein R has the formula:

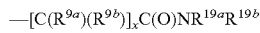

$R^{19a}$ and $R^{19b}$ are each independently hydrogen, methyl, or ethyl; $R^{9a}$ and $R^{9b}$ are each independently hydrogen or methyl; the index x is from 0 to 2.

11. The compound according to claim 1, wherein $R^1$ is chosen from:
a) hydrogen;
b) substituted or unsubstituted $C_1$-$C_4$ linear, branched, or cyclic alkyl;
c) —$[CH_2]_xOR^{20}$; and
  $R^{20}$ is chosen from:
  i) hydrogen;
  ii) substituted or unsubstituted $C_1$-$C_4$ linear, branched, or cyclic alkyl; and
  iii) —$C(O)R^{21}$; $R^{21}$ is chosen from hydrogen; $C_1$-$C_4$ linear, branched, or cyclic alkyl; substituted or unsubstituted phenyl; or substituted or unsubstituted benzyl; or
d) —$[CH_2]_xC(O)R^{22}$;
  $R^{22}$ is chosen from:
  i) substituted or unsubstituted $C_1$-$C_4$ linear, branched, or cyclic alkyl;
  ii) —$OR^{23}$; $R^{23}$ is chosen from hydrogen; substituted or unsubstituted $C_1$-$C_4$ linear, branched, or cyclic alkyl; substituted or unsubstituted phenyl; or substituted or unsubstituted benzyl.

12. The compound according to claim 1, wherein $R^2$ is hydrogen and $R^3$ is hydroxyl or halogen.

13. The compound according to claim 1, wherein $R^2$ is hydrogen and $R^3$ is hydroxyl.

14. The compound according to claim 1, wherein $R^3$ is hydrogen and $R^2$ is hydroxyl or halogen.

15. The compound according to claim 1, wherein $R^3$ is hydrogen and $R^2$ is hydroxyl.

16. The compound according to claim 1, wherein $R^2$ and $R^3$ are both hydroxyl.

17. The compound according to claim 1, wherein $R^4$ has the formula:

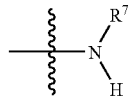

$R^7$ is chosen from:
a) hydrogen; and
b) —$C(O)R^{30}$;
  $R^{30}$ is chosen from:
  i) substituted or unsubstituted $C_1$-$C_4$ linear, branched, or cyclic alkyl;
  ii) —$OR^{31}$; $R^{31}$ is chosen from substituted or unsubstituted $C_1$-$C_4$ linear or branched alkyl; or benzyl; and
  iii) substituted or unsubstituted benzyl.

18. The compound according to claim 1, wherein $R^5$ is hydrogen and $R^6$ is chosen from:
a) substituted or unsubstituted $C_1$-$C_{12}$ linear or branched alkyl;
b) —$[CH_2]_xR^{40}$;
  $R^{40}$ is chosen from:
  i) substituted or unsubstituted phenyl;
  ii) substituted or unsubstituted $C_1$-$C_9$ heterocyclic; and
  ii) substituted or unsubstituted $C_1$-$C_9$ heteroaryl;
  iv) —$N(R^{41a})(R^{41b})$; $R^{41a}$ and $R^{41b}$ are each independently hydrogen or methyl;
c) —$[CH_2]_xC(=R^{43})R^{42}$; and
  $R^{41}$ is chosen from
  i) —$N(R^{44a})(R^{44b})$; and
    $R^{44a}$ and $R^{44b}$ are each independently hydrogen or methyl;
  ii) —$OR^{45}$;
    $R^{45}$ is hydrogen or methyl;
  $R^{43}$ is O or NH;
d) —$[CH_2]_xNHC(=R^{47})R^{46}$;
  $R^{46}$ is —$N(R^{48a})(R^{48b})$; $R^{48a}$ and $R^{48b}$ are each independently hydrogen or methyl;
  $R^{47}$ is O or NH;
  the index x is from 0 to 4.

19. The compound according to claim 1, wherein $R^6$ is hydrogen and $R^5$ is chosen from:
a) substituted or unsubstituted $C_1$-$C_{12}$ linear or branched alkyl;
b) —$[CH_2]_xR^{40}$;
  $R^{40}$ is chosen from:
  i) substituted or unsubstituted phenyl;
  ii) substituted or unsubstituted $C_1$-$C_9$ heterocyclic; and
  ii) substituted or unsubstituted $C_1$-$C_9$ heteroaryl;
  iv) —$N(R^{41a})(R^{41b})$; $R^{41a}$ and $R^{41b}$ are each independently hydrogen or methyl;
c) —$[CH_2]_xC(=R^{43})R^{42}$; and
  $R^{41}$ is chosen from
  i) —$N(R^{44a})(R^{44b})$;
    $R^{44a}$ and $R^{44b}$ are each independently hydrogen or methyl; and
  ii) —$OR^{45}$;
    $R^{45}$ is hydrogen or methyl;
  $R^{43}$ is O or NH;
d) —$[CH_2]_xNHC(=R^{47})R^{46}$;
  $R^{46}$ is —$N(R^{48a})(R^{48b})$; $R^{48a}$ and $R^{48b}$ are each independently hydrogen or methyl;
  $R^{47}$ is O or NH;
  the index x is from 0 to 4.

20. The compound according to claim 1, wherein said substitutions are each independently chosen from:
i) $C_1$-$C_{12}$ linear, branched, or cyclic alkyl, alkenyl, and alkynyl;
ii) substituted or unsubstituted $C_6$ or $C_{10}$ aryl;

iii) substituted or unsubstituted $C_1$-$C_9$ heterocyclic rings;
iv) substituted or unsubstituted $C_1$-$C_9$ heteroaryl rings;
v) —$(CR^{52a}R^{52b})_zOR^{51}$;
vi) —$(CR^{52a}R^{52b})_zC(O)R^{51}$;
vii) —$(CR^{52a}R^{52b})_zC(O)OR^{51}$;
viii) —$(CR^{52a}R^{52b})_zC(O)N(R^{51})_2$;
ix) —$(CR^{52a}R^{52b})_zN(R^{51})_2$;
x) halogen;
xi) —$(CR^{52a}R^{52b})_zCN$;
xii) —$(CR^{52a}R^{52b})_zNO_2$;
xiii) —$CH_jQ_k$; wherein Q is halogen, j is from 0 to 2, j+k=3;
xiv) —$(CR^{52a}R^{52b})_zSR^{51}$;
xv) —$(CR^{52a}R^{52b})_zSO_2R^{51}$; and
xiii) —$(CR^{52a}R^{52b})_zSO_3R^{51}$;
wherein each $R^{51}$ is independently hydrogen, substituted or unsubstituted $C_1$-$C_4$ linear, branched, or cyclic alkyl; or two $R^{51}$ units can be taken together to form a ring comprising 3-7 atoms; $R^{52a}$ and $R^{52b}$ are each independently hydrogen or $C_1$-$C_4$ linear or branched alkyl; the index p is from 0 to 4.

21. A compound, or pharmaceutically acceptable salt thereof, having the formula:

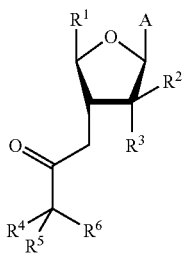

wherein A is a substituted or unsubstituted $C_5$-$C_8$ heteroaryl unit;
$R^1$ is a unit having the formula:
—$[C(R^{9a})(R^{9b})]_xOC(O)R^{21}$
wherein $R^{9a}$ and $R^{9b}$ are each independently hydrogen or methyl; the index x is from 0 to 3; and
$R^{21}$ is chosen from hydrogen, methyl, phenyl, or benzyl;
$R^2$ is hydrogen or hydroxyl;
$R^3$ is hydrogen or hydroxyl;
$R^4$ is has the formula chosen from:

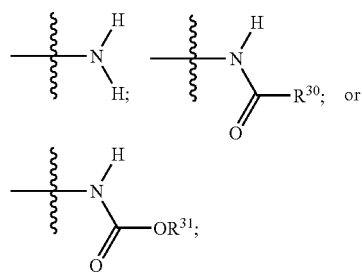

$R^{30}$ is chosen from methyl, ethyl, tert-butyl, phenyl, and benzyl;
$R^{31}$ is chosen from methyl, ethyl, tert-butyl, and benzyl;
$R^5$ and $R^6$ are each independently:
i) —$CH_3$;
ii) —$CH(CH_3)_2$;
iii) —$CH_2CH(CH_3)_2$;
iv) —$CH(CH_3)CH_2CH_3$;
v) —$CH_2OH$;
vi) —$CHOHCH_3$;
vii) —$CH_2SH$;
viii) —$CH_2SCH_3$;
ix) substituted aryl having the formula:

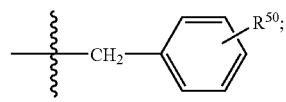

x) substituted heteroaryl:
i) imidazol-4-yl having the formula:

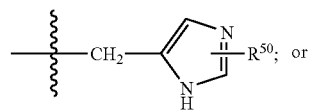

ii) indol-3-yl having the formula:

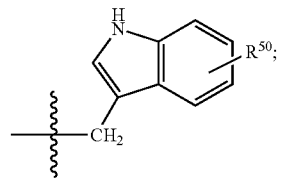

xi) —$CH_2CO_2H$;
xii) —$CH_2CH_2CO_2H$;
xiii) —$CH_2CONH_2$;
xiv) —$CH_2CH_2CONH_2$; and
xv) —$CH_2NHC(NH)NH_2$;
$R^{50}$ is one or more optional substitutions for hydrogen.

22. The compound according to claim 21, wherein A is chosen from 1H-indolyl, 1H-pyrrolo[2,3-b]pyridinyl, 7H-pyrrolo[2,3-d]pyrimidinyl, 5H-pyrrolo[2,3-b]pyrazinyl, 7H-pyrrolo[2,3-c]pyridazinyl, 5H-pyrrolo[3,2-c]pyridazinyl, 1H-benzo[d]imidazolyl, 7H-imidazo[4,5-c]pyridazinyl, 1H-imidazo[4,5-b]pyrazinyl, 7H-purinyl, 9H-purinyl, quinolin-2-yl, quinolin-3-yl, quinolin-4-yl, isoquinolin-1-yl, isoquinolin-3-yl, and isoquinolin-4-yl.

23. A compound, or pharmaceutically acceptable salts thereof, having the formula:

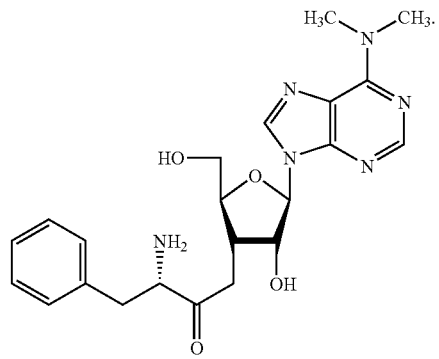

* * * * *